US007811822B2

(12) United States Patent
Lindquist et al.

(10) Patent No.: US 7,811,822 B2
(45) Date of Patent: Oct. 12, 2010

(54) MODULATION OF NEURAL STEM CELLS AND NEURAL PROGENITOR CELLS

(75) Inventors: Per Lindquist, Bromma (SE); Alex Mercer, Bromma (SE); Harriet Rönnholm, Trångsund (SE); Lilian Wikström, Spånga (SE)

(73) Assignee: NeuroNova AB, Stockholm (SE)

( * ) Notice: Subject to any disclaimer, the term of this patent is extended or adjusted under 35 U.S.C. 154(b) by 196 days.

(21) Appl. No.: 11/880,213

(22) Filed: Jul. 19, 2007

(65) Prior Publication Data

US 2008/0213276 A1 Sep. 4, 2008

Related U.S. Application Data

(63) Continuation of application No. 10/434,943, filed on May 8, 2003, now abandoned.

(60) Provisional application No. 60/379,114, filed on May 8, 2002, provisional application No. 60/393,159, filed on Jul. 2, 2002.

(51) Int. Cl.
*C12N 5/00* (2006.01)
*C12N 5/074* (2006.01)
*C12N 5/0797* (2006.01)

(52) U.S. Cl. .................. 435/377; 435/325; 435/368; 514/114

(58) Field of Classification Search .................. None
See application file for complete search history.

(56) References Cited

U.S. PATENT DOCUMENTS

| | | | |
|---|---|---|---|
| 4,522,811 | A | 6/1985 | Eppstein et al. |
| 4,692,147 | A | 9/1987 | Duggan |
| 5,011,678 | A | 4/1991 | Wang et al. |
| 5,166,322 | A | 11/1992 | Shaw et al. |
| 5,254,330 | A | 10/1993 | Ganderton et al. |
| 5,670,477 | A | 9/1997 | Poduslo et al. |
| 5,712,262 | A * | 1/1998 | Spiegel ....................... 514/114 |
| 5,766,897 | A | 6/1998 | Braxton |
| 5,832,932 | A | 11/1998 | Elsberry et al. |
| 6,004,565 | A | 12/1999 | Chiba et al. |
| 6,042,579 | A | 3/2000 | Elsberry et al. |
| 6,380,177 | B1 | 4/2002 | Erickson |
| 6,420,339 | B1 | 7/2002 | Gegg et al. |
| 6,476,004 | B1 | 11/2002 | Sakai et al. |
| 6,552,170 | B1 | 4/2003 | Thompson et al. |
| 2003/0165485 | A1 | 9/2003 | Bertilsson et al. |
| 2003/0203844 | A1 | 10/2003 | Delfani et al. |
| 2004/0014662 | A1 | 1/2004 | Lindquist et al. |
| 2004/0038888 | A1 | 2/2004 | Mercer et al. |
| 2004/0048377 | A1 | 3/2004 | Ericson |
| 2005/0090520 | A1 | 4/2005 | Lindquist |

FOREIGN PATENT DOCUMENTS

| | | |
|---|---|---|
| EP | 0812588 | 12/1997 |
| WO | WO 94/08943 | 4/1994 |
| WO | WO 99/19513 | 4/1999 |
| WO | WO 99/36065 | 7/1999 |
| WO | WO 00/09139 | 2/2000 |
| WO | WO 03/094965 | 11/2003 |
| WO | WO 2004/028521 | 4/2004 |
| WO | WO 2005/002559 | 1/2005 |
| WO | WO 2005/025553 | 3/2005 |

OTHER PUBLICATIONS

Chun et al. (2002) Pharmacological Reviews 54: 265-269.*
Harada et al. (2001). Society for Neuroscience Abstracts 27: 933. Database Biosis, Accession No. PREV200100498277.*
Nam et al. (2001). Society for Neuroscience Abstracts 2._77: 1235. Database Biosis, Accession No. PREV200100549552.*
Yoshida and Ueda (2001). Jpn. J. Pharmacol. 87: 104-109.*
Colucci-D'Amato and Di Porzio (BioEssays 30:135-145, 2008).*
Adachi et al., "Design, synthesis and structure-activity relationships of 2-substituted-2-amino-1,3-propanediols: Discovery of a novel immunosuppressant, FTY720." Bioorganic and Medicinal Chemistry Letters 5(8): 853-856 (1995).
Altman and Das, "Autoradiographic and histological evidence of postnatal hippocampal neurogenesis in rats." J Comp Neurol 124: 319-335 (1965).
Altman and Das, "Postnatal neurogenesis in the guinea-pig." Nature 214: 1098-1101 (1967).
An et al., "Identification of cDNAs encoding two G protein-coupled receptors for lysosphingolipids." FEBS Lett. 417(3):279-82 (1997).
An et al., "Characterization of a novel subtype of human G protein-coupled receptor for lysophosphatidic acid." J Biol Chem. 273(14):7906-10. (1998).
An et al., "Sphingosine 1-phosphate-induced cell proliferation, survival, and related signaling events mediated by G protein-coupled receptors Edg3 and Edg5." J Biol Chem. 275(1):288-96 (2000).
Anliker and Chun, Lysophospholipid G protein-coupled receptors. J Biol Chem. 279(20): 20555-8 (2004).
Aoki et al., "A novel human G-protein-coupled receptor, EDG7, for lysophosphatidic acid with unsaturated fatty-acid moiety." Ann N Y Acad Sci. 905:263-6 (2000).
Ballmaier M et al., " Preferential alterations in the mesolimbic dopamine pathway of heterozygous reeler mice: an emerging animal-based model of schizophrenia." Eur J Neurosci 15: 1197-205 (2002).
Bayer S.A., "Neurogenesis in the rat primary olfactory cortex." Int J Dev Neurosci. 4(3):251-71 (1986).
Beer et al., "EDG receptors as a therapeutic target in the nervous system." Ann N Y Acad Sci. 905: 118-31 (2000).

(Continued)

*Primary Examiner*—Gary B. Nickol
*Assistant Examiner*—Daniel C Gamett
(74) *Attorney, Agent, or Firm*—Mintz Levin Cohn Ferris Glovsky and Popeo, P.C.; Ivor R. Elrifi; Matthew Pavao

(57) ABSTRACT

The invention relates generally to methods of influencing central nervous system cells to produce progeny useful in the treatment of CNS disorders. More specifically, the invention includes methods of exposing a patient suffering from such a disorder to a reagent that modulates the proliferation, migration, differentiation and survival of central nervous system cells via S1P or LPA signaling. These methods are useful for reducing at least one symptom of the disorder.

9 Claims, 9 Drawing Sheets

OTHER PUBLICATIONS

Bernier et al., "Newly generated neurons in the amygdala and adjoining cortex of adult primates."Proc Natl Acad Sci U S A. 99(17):11464-9 (2002).
Biebl et al., "Analysis of neurogenesis and programmed cell death reveals a self- renewing capacity in the adult rat brain." Neurosci Lett 291(1): 17-20 (2000).
Billinton et al., "GABA(B(1)) splice variant mRNAs are differentially affected by electroshock induced seizure in rats." Neuroreport 11(17):3817-22 (2000).
Björklund and Lindvall, "Cell replacement therapies for central nervous system disorders." Nat Neurosci. 3(6):537-44 (2000).
Borison and Diamond, "A new animal model for schizophrenia: interactions with adrenergic mechanisms." Biol Psychiatry 13(2):217-25 (1978).
Born et al.,"Sniffing neuropeptides: a transnasal approach to the human brain." Nat Neurosci 5(6): 514-6 (2002).
Brinkmann et al, "FTY720: altered lymphocyte traffic results in allograft protection." Transplantation. 72(5):764-9 (2001).
Brinkmann et al, "The immune modulator FTY720 targets sphingosine 1-phosphate receptors." J Biol Chem. 277(24): 21453-7 (2002).
Broekkamp et al., "Major tranquillizers can be distinguished from minor tranquillizers on the basis of effects on marble burying and swim-induced grooming in mice." Eur J Pharmacol 126(3):223-9 (1986).
Chae et al., "Constitutive expression of the S1P1 receptor in adult tissues." Prostaglandins Other Lipid Mediat. 73, 141-50 (2004).
Chen et al., "Free thoracodorsal artery perforator flap in extremity reconstruction: 12 cases." Br J Plast Surg. 57, 525-30 (2004).
Chiba et al., "FTY720, a novel immunosuppressant, induces sequestration of circulating lymphocytes by acceleration of lymphocyte homing." Transplant Proc. 31, 1230-3 (1999).
Chun, "Lysophospholipid receptors: implications for neural signaling." Crit Rev Neurobiol. 13, 151-68 (1999).
Chun et al., "International Union of Pharmacology. XXXIV. Lysophospholipid receptor nomenclature." Pharmacol Rev. 54(2):265-9. (2002).
Colthorpe et al., "The pharmacokinetics of pulmonary-delivered insulin: a comparison of intratracheal and aerosol administration to the rabbit." Pharm Res. Jun; 9(6):764-8 (1992).
Colucci-D'Amato and di Porzio, "Neurogenesis in adult CNS: from denial to opportunities and challenges for therapy." Bioessays. 30(2):135-45 (2008).
Contos et al., "Requirement for the lpA1 lysophosphatidic acid receptor gene in normal suckling behavior." Proc Natl Acad Sci U S A. 97(24):13384-9 (2000).
Craig et al., "In vivo growth factor expansion of endogenous subependymal neural precursor cell populations in the adult mouse brain." J Neurosci 16(8): 2649-58 (1996).
Crouch et al., "The use of ATP bioluminescence as a measure of cell proliferation and cytotoxicity." J Immunol Methods. 160, 81-8 (1993).
Czlonkowska et al., "Immune processes in the pathogenesis of Parkinson's disease—a potential role for microglia and nitric oxide." Med Sci Monit. 8(8): RA165-77 (2002).
Doetsch et al., "Cellular composition and three-dimensional organization of the subventricular germinal zone in the adult mammalian brain." J Neurosci. 17(13):5046-61 (1997).
Doetsch et al., "Subventricular zone astrocytes are neural stem cells in the adult mammalian brain." Cell 97(6): 703-16 (1999).
Edsall et al., "Involvement of sphingosine 1-phosphate in nerve growth factor-mediated neuronal survival and differentiation." J. Neurosci 17(18): 6952-6960 (1997).
Ekdahl et al., "Inflammation is detrimental for neurogenesis in adult brain." Proc Natl Acad Sci U S A. 100(23): 13632-7 (2003).
Elliott et al., "Parenteral absorption of insulin from the lung in diabetic children." Aust Paediatr J 23,293-297 (1987).
Fiore M et al., "Prenatal methylazoxymethanol acetate alters behavior and brain NGF levels in young rats: a possible correlation with the development of schizophrenia-like deficits." Neuropharmacology 38(6):857-69 (1999).

Fitzgerald et al., "Identification of an EDG7 variant, HOFNH30, a G-protein-coupled receptor for lysophosphatidic acid." Biochem Biophys Res Commun. 273(3):805-10 (2000).
Fujino et al., "Amelioration of experimental autoimmune encephalomyelitis in Lewis rats by FTY720 treatment." J Pharmacol Exp Ther. 305(1): 70-7 (2003).
Fukushima et al., "Neurobiology of lysophosphatidic acid signaling."Neuroscientist. 8(6):540-50 (2002).
Fukushima and Chun, "The LPA receptors." Prostaglandins Other Lipid Mediat. 64(1-4):21-32 (2001).
Fukushima et al., "Lysophospholipid receptors." Annu Rev Pharmacol Toxicol, 41, 507-34 (2001).
Gage et al., "Multipotent progenitor cells in the adult dentate gyrus." J Neurobiol. 36(2):249-66 (1998).
Gamaniel et al., "Effects of iloprost, prostaglandin E1 (PGE1) and prostacyclin (PGI2) on chemically and electrically induced seizures in mice." Prostaglandins Leukot Essent Fatty Acids 35(2): 63-8 (1989).
Gansslen, "Über Inhalation von Insulin." Klin Wochenschr; 4:71 (1925).
Glickman et al., "Molecular cloning, tissue-specific expression, and chromosomal localization of a novel nerve growth factor-regulated G-protein-coupled receptor, nrg-1." Mol Cell Neurosci. 14, 141-52 (1999).
Goetzl and An, "Diversity of cellular receptors and functions for the lysophospholipid growth factors lysophosphatidic acid and sphingosine 1-phosphate." FASEB J. 12(15):1589-98 (1998).
Goetzl et al., "Dual mechanisms for lysophospholipid induction of proliferation of human breast carcincrna cells." Cancer Res. 59(18):4732-7 (1999).
Govinda, "Aerosol Insulin Inhalation Inquiry" Indian J. Physiol. Pharmacol. 3:161-167 (1959).
Gräler et al., "EDG6, a novel G-protein-coupled receptor related to receptors for bioactive lysophospholipids, is specifically expressed in lymphoid tissue." Genomics. 53(2):164-9 (1998).
Hale et al., "Potent SIP receptor agonists replicate the pharmacologic actions of the novel immune modulator FTY720." Bioorg Med Chem Lett. 14, 3351-5 (2004).
Harada et al. Society for Neuroscience Abstracts 27: 933 (2001). Database Biosis, Accession No. PREV200100498277.
Harada et al., "Sphingosine-1-phosphate induces proliferation and morphological changes of neural progenitor cells." J Neurochem. 88, 1026-39 (2004).
Hastings et al., "Clearance of different-sized protein from the alveolar space in humans and rabbits." J Appl Physiol 73:1310-1316 (1992).
Hecht et al., "Ventricular zone gene-1 (vzg-1) encodes a lysophosphatidic acid receptor expressed in neurogenic regions of the developing cerebral cortex." J Cell Biol. 135(4):1071-83 (1996).
Herman and Abrous, "Dopaminergic neural grafts after fifteen years: results and perspectives."Prog Neurobiol. 44(1):1-35 (1994).
Hisanaga et al., "Increase in peripheral CD4 bright+ CD8 dull+ T cells in Parkinson disease." Arch Neural. 58, 1580-3 (2001).
Hla and Maciag, "An abundant transcript induced in differentiating human endothelial cells encodes a polypeptide with structural similarities to G-protein-coupled receptors." J Biol Chem. 265(16):9308-13 (1990).
Holmes et al., "Behavioral characterization of dopamine D5 receptor null mutant mice." Behav Neurosci 115(5):1129-44 (2001).
Im et al., "Characterization of the human and mouse sphingosine 1-phosphate receptor, SIP5 (Edg-8): structure-activity relationship of sphingosine1-phosphate receptors." Biochemistry. 40, 14053-60 (2001).
Im et al., "Characterization of a novel sphingosine 1-phosphate receptor, Edg-8." J Biol Chem. 275(19):14281-6 (2000).
Jacobson, "Histosenesis and morphogenesis of cortical structures." Developmental Neurobiology, Plenum Press, New York: 401-451 (1991).
Jalink et al., "Lysophosphatidic acid induces neuronal shape changes via a novel, receptor-mediated signaling pathway: similarity to thrombin action." Cell Growth Differ. 4(4):247-55 (1993).
Johansson et al., "Neural stem cells in the adult human brain." Exp Cell Res 253(2): 733-6 (1999).

Johansson et al., "Identification of a neural stem cell in the adult mammalian central nervous system." Cell 96(1): 25-34 (1999).

Johe et al., "Single factors direct the differentiation of stem cells from the fetal and adult central nervous system." Genes Dev 10(24): 3129-40 (1996).

Kaneider et al., "The immune modulator FTY720 targets sphingosine-kinase-dependent migration of human monocytes in response to amyloid beta-protein and its precursor." FASEB Journal 18(11): 1309-1311 (2004).

Kennel et al., "Riluzole prolongs survival and delays muscle strength deterioration in mice with progressive motor neuronopathy (pmn)." J Neurol Sci 180(1-2):55-61 (2000).

Kiuchi et al., "Synthesis and immunosuppressive activity of 2-substituted 2-aminopropane-1,3-diols and 2-aminoethanols." Journal of Medicinal Chemistry 43(15): 2946-2961 (2000).

Krugel et al., "Deafferentation of the septo-hippocampal pathway in rats as a model of the metabolic events in Alzheimer's disease." Int J Dev Neurosci 19(3):263-77 (2001).

Kuhn and Svendsen, "Origins, functions, and potential of adult neural stem cells." Bioessays 21(8): 625-30 (1999).

Kuhn et al., "Epidermal growth factor and fibroblast growth factor-2 have different effects on neural progenitors in the adult rat brain." J Neurosci. 17(15):5820-9 (1997).

Laube, "Preliminary study of insulin aerosol delivered by oral inhalation in diabetic patients." JAMA 269(16): 2106-9 (1993).

Lee and Sciarra, "Development of an aerosol dosage form containing insulin." J. Pharm. Sci. 65(4): 567-572 (1976).

Lee et al., "FTY720 induces apoptosis of human hepatoma cell lines through PI3-K-mediated Akt dephosphorylation." Carcinogenesis 25(12): 2397-2405 (2004).

Lee et al., "Sphingosine-1-phosphate as a ligand for the G protein-coupled receptor EDG-1." Science. 279(5356):1552-5 (1998).

Liu et al,, "Edg-1, the G protein-coupled receptor for sphingosine-1-phosphate, is essential for vascular maturation." J Clin Invest. 106(8): 951-61 (2000).

Lois and Alvarez-Buylla, "Proliferating subventricular zone cells in the adult mammalian forebrain can differentiate into neurons and glia." Proc Natl Acad Sci U S A 90(5): 2074-7 (1993).

Magavi et al., "Induction of neurogenesis in the neocortex of adult mice." Nature 405(6789): 951-5 (2000).

Maki et al., "Prevention of autoimmune diabetes by FTY720 in nonobese diabetic mice." Transplantation 74(12): 1684-6 (2002).

Mandala et al., "Alteration of lymphocyte trafficking by sphingosine-1-phosphate receptor agonists." Science 296, 346-9 (2002).

Marco et al., "Striatopallidal neurons are selectively protected by neurturin in an excitotoxic model of Huntington's disease." J Neurobiol 50(4):323-32 (2002).

Masubuchi et al., "FTY12, a novel immunosuppressant, possessing unique mechanisms. IV. Prevention of graft versus host reactions in rats." Transplant Proc. 28(2): 1064-5 (1996).

Matsuura et al., "Effect of FTY720, a novel immunosuppressant, on adjuvant- and collagen-induced arthritis in rats" Int J Immunopharmacol. 22, 323-31 (2000).

Matsuura et al., "Effect of FTY720, a novel immunosuppressant, on adjuvant-induced arthritis in rats." Inflamm Res. 49, 404-10 (2000).

McGiffert et al., "Embryonic brain expression analysis of lysophospholipid receptor genes suggests roles for s1p(1) in neurogenesis and s1p(1-3) in angiogenesis." FEBS Lett. 531(1):103-8 (2002).

McKay, "Stem cells in the central nervous system." Science 276(5309): 66-71 (1997).

McLennan et al., "Antisense studies in PC-12 cells suggest a role for H218, a sphingosine 1-phosphate receptor, in growth factor-induced cell-cell interaction and neurite outgrowth." Developmental Neuroscience 22(4): 283-295 (2000).

Menalled and Chesselet, "Mouse models of Huntington's disease." Trends Pharmacol Sci. 23(1):32-9 (2002).

Momma et al., "Get to know your stem cells." Cuff Opin Neurobiol 10(1): 45-9 (2000).

Moyse et al., "Short- and long-term effects of nucleus basalis magnocellularis lesions on cortical levels of somatostatin and its receptors in the rat." Brain Res 607(1-2):154-60 (1993).

Nagai et al., "Powder Dosage Form of Insulin for Nasal Administration" J. Contr. Rel. 1:15-22 (1984).

Nagano et al., "New Method of Insulin Therapy: Transpulmonary Absorption of Insulin" Jikeikai Med. J. 32:503506 (1985).

Nam et al. *Society for Neuroscience Abstracts* 27: 1235 (2001). Database Biosis, Accession No. PREV200100549552.

O'Connor et al., "Behavioural and neuropharmacological properties of the dibenzazepines, desipramine and lofepramine: studies on the olfactory bulbectomized rat model of depression." Prog Neuropsychopharmacol Biol Psychiatry 12(1):41-51 (1988).

O'Dell and Marshall, "Chronic L-dopa alters striatal NMDA receptors in rats with dopaminergic injury." Neuroreport (1996) 7(15-17):2457-61 (1996).

Palmer et al., "Fibroblast growth factor-2 activates a latent neurogenic program in neural stem cells from diverse regions of the adult CNS." J Neurosci 19(19): 8487-97 (1999).

Pébay, et al., "Sphingosine-1-phosphate induces proliferation of astrocytes: regulation by intracellular signalling cascades." Eur J Neurosci. 13(12):2067-76 (2001).

Pela et al., "Evidence that platelet-derived-growth-factor may be a novel endogenous pyrogen in the central nervous system." Am. J. Physiol. Regul. Integr. Comp. Physiol. 278:R1275-81 (2000).

Pelleymounter et al., "Pharmacological evidence supporting a role for central corticotropin-releasing factor(2) receptors in behavioral, but not endocrine, response to environmental stress." J Pharmacol Exp Ther 302(1):14552 (2002).

Pencea et al., "Infusion of Brain-Derived Neurotrophic Factor into the Lateral Ventricle of the Adult Rat Leads to New Neurons in the Parenchyma of the Striatum, Septum, Thalamus, and Hypothalamus." J Neurosci 21(17): 6706-17 (2001).

Postma et al., "Sphingosine-1-phosphate rapidly induces Rho-dependent neurite retraction: action through a specific cell surface receptor." EMBO J. 15(10):2388-92 (1996).

Pyne and Pyne, "Sphingosine 1-phosphate signalling in mammalian cells." Biochem J. 349(Pt 2):385-402 (2000).

Pyne and Pyne, "Sphingosine 1-phosphate signalling via the endothelial differentiation gene family of G-protein-coupled receptors." Pharmacol Ther. 88(2):115-31 (2000).

Radeff-Huang et al., "G protein mediated signaling pathways in lysophospholipid induced cell proliferation and survival." J Cell Biochem. 92, 949-66 (2004).

Rajan and McKay, "Multiple routes to astrocytic differentiation in the CNS." J Neurosci 18(10): 3620-9 (1998).

Riban et al., "Evolution of hippocampal epileptic activity during the development of hippocampal sclerosis in a mouse model of temporal lobe epilepsy." Neuroscience 112(1):101-11 (2002).

Rius et al., "Activation of sphingosine kinase in pheochromocytoma PC12 neuronal cells in response to trophic factors." FEBS Lett. 417(2):173-6 (1997).

Roof et al., "A comparison of long-term functional outcome after 2 middle cerebral artery occlusion models in rats." Stroke 32(11):2648-57 (2001).

Sakr, "A new approach for insulin delivery via the pulmonary route: Design and pharmacokinetics in non-diabetic rabbits." Int. J. Phar. 86:1-7 (1992).

Sanchez and Hla, "Structural and functional characteristics of S1P receptors." J Cell Biochem. 92, 913-22 (2004).

Sautin et al., "Hepatic oval (stem) cell expression of endothelial differentiation gene receptors for lysophosphatidic acid in mouse chronic liver injury." J Hematother Stem Cell Res. 11(4):643-9 (2002).

Schenk and Morris, "Dissociation between components of spatial memory in rats after recovery from the effects of retrohippocampal lesions." Exp Brain Res 58(1):11-28 (1985).

Schluter et al., "Pulmonary administration of human insulin in volunteers and typo-I diabetics." Diabetes 33:75A (1984). (Abstract Only).

Schmidt and Ferger, "Neurochemical findings in the MPTP model of Parkinson's disease." J Neural Transm 108(11):1263-82 (2001).

Schwarz et al., "Identification of differentially expressed genes induced by transient ischemic stroke." Brain Res Mol Brain Res 101(1-2):12-22 (2002).

Shinomiya et al., "An immunosuppressive agent, FTY720, increases intracellular concentration of calcium ion and induces apoptosis in HL-60." Immunology. 91, 594-600 (1997).

Shirayama et al., "Brain-derived neurotrophic factor produces antidepressant effects in behavioral models of depression." J Neurosci 22(8):3251-61 (2002).

Snyder et al., "Multipotent neural precursors can differentiate toward replacement of neurons undergoing targeted apoptotic degeneration in adult mouse neocortex." Proc Natl Acad Sci USA 94(21):11663-8 (1997).

Spiegel and Kolesnick, "Sphingosine 1-phosphate as a therapeutic agent" Leukemia. 16(9):1596-602 (2002).

Talamini et al., Brain Res 847(1):105-20 (1999).

Tedesco-Silva et al., "FTY720, a novel immunomodulator: efficacy and safety results from the first phase 2A study in de novo renal transplantation." Transplantation. 77(12):1826-33 (2004).

Tiedtke et al., "MK-801-induced stereotypy and its antagonism by neuroleptic drugs." J Neural Transm Gen Sect 8I(3):173-82 (1990).

Tigyi et al., "Lysophosphatidic acid possesses dual action in cell proliferation." Proc Natl Acad Sci U S A. 91(5):1908-12 (1994).

Toman and Spiegel, "Lysophospholipid receptors in the nervous system." Neurochem Res. 27(7-8):619-27 (2002).

Uhlenbrock et al., "Sphingosine 1-phosphate is a ligand of the human gpr3, gpr6 and gpr12 family of constitutively active G protein-coupled receptors." Cell Signal. Nov. 2002;14(11):941-53 (2002).

Usui et al., "Blood lipid mediator sphingosine 1-phosphate potently stimulates platelet-derived growth factor-A and -B chain expression through S1P1-Gi-Ras-MAPK-dependent induction of Kruppel-like factor 5." J Biol Chem. 279(13): 12300-11 (2004).

Webb et al., "Sphingosine 1-phosphate receptor agonists attenuate relapsing-remitting experimental autoimmune encephalitis in SJL mice." 3 Neuroimmunol. 153, 108-21 (2004).

Weiner et al., "Lysophosphatidic acid receptor gene vzg-1/lpA1/edg-2 is expressed by mature oligodendrocytes during myelination in the postnatal murine brain." J Comp Neurol. 398(4):587-98 (1998).

Williams et al., "A PDGF-regulated immediate early gene response initiates neuronal differentiation in ventricular zone progenitor cells." Neuron 18(4): 553-62 (1997).

Yagita et al., "Neurogenesis by progenitor cells in the ischemic adult rat hippocampus." Stroke 32(8):1890-6 (2001).

Yamazaki et al., "Edg-6 as a putative sphingosine 1-phosphate receptor coupling to Ca(2+) signaling pathway." Biochem Biophys Res Commun 268(2): 583-9 (2000).

Yang at al., "The immune modulator FYT720 prevents autoimmune diabetes in nonobese diabetic mice small star, filled." Clin Immunol. 107, 30-5 (2003).

Yoshida and Ueda, "Activation of Gi1 by lysophosphatidic acid receptor without ligand in the baculovirus expression system." Biochem Biophys Res Commun. 259(1):78-84. (1999).

Yoshida and Ueda, "Neurobiology of the Edg2 lysophosphatidic acid receptor." Jpn J Pharmacol. 87(2):104-9. (2001).

Zhang et al., "Comparative analysis of three murine G-protein coupled receptors activated by sphingosine-1-phosphate." Gene. 227, 89-99 (1999).

Zwick at al., "The EGF receptor as central transducer of heterologous signalling systems." Trends Pharmacol Sci. 20(10):408-12 (1999).

International Searching Authority Re.: Application No. PCT/IB03/02370 International Search Report Dated Apr. 23, 2004.

International Searching Authority Re.: Application No. PCT/IB3/2004/003288 International Search Report Dated Mar. 11, 2005.

European Patent Office Re.: Application No. 04787557.0 Communication Pursuant to Article 94(3) EPC Dated Apr. 26, 2007.

* cited by examiner

BrdU POS CELLS IN STRIATUM

```
                        SEQUENCE LISTING

<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaaccaaga agttccaccg gccc                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgccttgcag cccacatcta acagt                                         25

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagctgcctc tacttccagc cctgtaattt                                    30

<210> SEQ ID NO 4
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
gatgactaca atcaccacca ccacgcga                                              28

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttcatcggc aacttggctc tctgc                                                 25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggacagccag catgatgaac cactg                                                 25

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgggccagt gctactacaa cgagacca                                              28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagaggcagt gccagaagtg tgcaggta                                              28

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggccttcgtg gccaacacct tact                                                  24

<210> SEQ ID NO 10
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 10
cccggctacg ccacgtatag atgac                                          25

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgaacatca gtacctggtc cacgctgg                                       28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcacagaccg atgcagccat acacac                                         26

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgaatgagtg tcactatgac aagcgcatgg                                     30

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttgcagagg caattccatc ccagc                                          25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggcgccggt gagtgaggtt attgt                                          25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic

```
                         -continued primer

<400> SEQUENCE: 16
aggcgtccta agcagttcca gccca                                        25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atggatgacg atatcgctgc gctgg                                        25

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtcatcttt tcacggttgg ccttagggt                                    29
```

MODULATION OF NEURAL STEM CELLS AND NEURAL PROGENITOR CELLS

RELATED APPLICATIONS

This application is a continuation of U.S. application Ser. No. 10/434,943, filed on May 8, 2003, now abandoned which claims the benefit of U.S. Ser. No. 60/379,114 filed May 8, 2002 and U.S. Ser. No. 60/393,159 filed Jul. 2, 2002. The entire teachings of the above applications are incorporated herein by reference.

FIELD OF THE INVENTION

The invention relates generally to methods of influencing adult neural stem cells and neural progenitor cells to produce progeny that can replace damaged or missing neurons or other central nervous system (CNS) cell types. More specifically, the invention includes methods of exposing a patient suffering from a disorder to a reagent that regulates the differentiation, proliferation, survival and migration of central nervous system cells via modulation of sphingosine-1-phosphate (S1P) or lysophosphatidic acid (LPA) signaling. These methods are useful for reducing at least one symptom of a neurological disorder.

BACKGROUND OF THE INVENTION

Throughout this specification, various patents, published patent applications and scientific references are cited to describe the state and content of the art. Those disclosures, in their entireties, are hereby incorporated into the present specification by reference.

For several years, it has been known that neural stem cells exist in the adult mammalian brain. This concept is of particular importance since the adult brain was thought to have very limited regenerative capacity. Moreover, the possibility to use adult-derived stem cells for tissue repair may help to overcome the ethical problems associated with embryonic cell research. Although the generation of neurons and glia can be observed in the adult brain, there is thus far only limited knowledge about stimulation of human neural stem cells in vitro and in vivo.

The first suggestions that new neurons were born in the adult mammalian brain came from studies performed in the 1960s (Altman and Das 1965; Altman and Das 1967). It however took another three decades and refined technical procedures to overthrow the dogma that neurogenesis within the mammalian CNS is restricted to embryogenesis and the perinatal period (for review see (Momma, Johansson et al. 2000); (Kuhn and Svendsen 1999)). Treatment of neural disease and injury traditionally focuses on keeping existing neurons alive, but possibilities now arise for exploiting neurogenesis for therapeutic treatments of neurological disorders and diseases.

The source of new neurons is neural stem cells (NSCs), located within the ependymal and/or subventricular zone (SVZ) lining the lateral ventricle (Doetsch, Caille et al. 1999; Johansson, Momma et al. 1999) and in the dentate gyrus of the hippocampus formation (Gage, Kempermann et al. 1998). Recent studies reveal the potential for several additional locations of NSC within the adult CNS (Palmer, Markakis et al. 1999). Asymmetric division of NSC maintain their number while generating a population of rapidly dividing precursor or progenitor cells (Johansson, Momma et al. 1999). The progenitors respond to a range of cues that dictate the extent of their proliferation and their fate, both in terms of the cell type that they differentiate into and the position that they ultimately take up in the brain.

The NSCs of the ventricular system in the adult are likely counterparts of the embryonic ventricular zone stem cells lining the neural tube whose progeny migrate away to form the CNS as differentiated neurons and glia (Jacobson 1991). NSCs persist in the adult lateral ventricle wall (LVW), generating neuronal progenitors which migrate down the rostral migratory stream to the olfactory bulb, where they differentiate into granule cells and periglomerular neurons (Lois and Alvarez-Buylla 1993). Substantial neuronal death occurs in the olfactory bulb generating a need for continuous replacement of lost neurons, a need satisfied by the migrating progenitors derived from the LVW (Biebl, Cooper et al. 2000). Further to this ongoing repopulation of olfactory bulb neurons, there are forceful indications that lost neurons from other brain regions can be replaced by progenitors from the LVW that differentiate into the lost neuron phenotype complete with appropriate neuronal projections and synapses with the correct target cell type (Snyder, Yoon et al. 1997; Magavi, Leavitt et al. 2000).

In vitro cultivation techniques have been established to identify the external signals involved in the regulation of NSC proliferation and differentiation (Johansson, Momma et al. 1999; Johansson, Svensson et al. 1999). The mitogens EGF and basic FGF allow neural progenitors, isolated from the ventricle wall and hippocampus, to be greatly expanded in culture (McKay 1997; Johansson, Svensson et al. 1999). The dividing progenitors remain in an undifferentiated state growing into large balls of cells known as neurospheres. Withdrawal of the mitogens combined with addition of serum induces differentiation of the progenitors into the three cell lineages of the brain: neurons, astrocytes and oligodendrocytes (Doetsch, Caille et al. 1999; Johansson, Momma et al. 1999). Application of specific growth factors can distort the proportions of each cell type in one way or another. For example, CNTF acts to direct the neural progenitors to an astrocytic fate (Johe, Hazel et al. 1996; Rajan and McKay 1998), while the thyroid hormone, triiodothyronine (T3) has been shown to promote oligodendrocyte differentiation (Johe, Hazel et al. 1996). Enhancement of neuronal differentiation of neural progenitors by PDGF has also been documented (Johe, Hazel et al. 1996; Williams, Park et al. 1997).

The ability to expand neural progenitor cells and then manipulate their cell fate has also had enormous implications in transplant therapies for neurological diseases in which specific cell types are lost. The most obvious example is Parkinson's Disease (PD) which is characterized by degeneration of dopaminergic neurons in the substantia nigra. Previous transplantation treatments for PD patients have used fetal tissue taken from the ventral midbrain at a time when substantia nigral dopaminergic neurons are undergoing terminal differentiation (Herman and Abrous 1994). The cells are grafted onto the striatum where they form synaptic contacts with host striatal neurons, their normal synaptic target, restoring dopamine turnover and release to normal levels with significant functional benefits to the patient (Herman and Abrous 1994) (for review see (Bjorklund and Lindvall 2000)). Grafting of fetal tissue is hindered by lack of donor tissue. In vitro expansion and manipulation of NSCs, however, can potentially provide a range of well characterized cells for transplant-based strategies for neurodegenerative diseases, such as dopaminergic cells for PD. To this aim, the identification of factors and pathways that govern the proliferation and differentiation of neural cell types will prove fundamental.

Ultimately the identification of these proliferative and differentiating factors is likely to provide insights into the stimulation of endogenous neurogenesis for the treatment of neurological diseases and disorders. Intraventricular infusion of both EGF and basic FGF have been shown to proliferate the ventricle wall cell population, and in the case of EGF, extensive migration of progenitors into the neighbouring striatal parenchyma (Craig, Tropepe et al. 1996; Kuhn, Winkler et al. 1997). The progenitors differentiated predominantly into a glial lineage while reducing the generation of neurons (Kuhn, Winkler et al. 1997). A recent study found that intraventricular infusion of BDNF in adult rats stimulates an increase in the number of newly generated neurons in the olfactory bulb and rostral migratory stream, and in parenchymal structures, including the striatum, septum, thalamus and hypothalamus (Pencea, Bingaman et al. 2001). These studies demonstrate that the proliferation of progenitors within the SVZ of the LVW can be stimulated and that their lineage can be manipulated to neuronal and glial fates. Currently the number of factors known to affect neurogenesis in vivo is small and their effects are either undesired or limited.

Therefore, there is a long felt need to identify other factors that can selectively stimulate neural stem cell activity through proliferation of neural progenitors and differentiation into the desired neuronal cell type. This activity would be beneficial for both stimulation of in vivo neurogenesis and culture of cells for transplantation therapy. The present invention demonstrates a role for S1P, LPA and their receptors in the proliferation, differentiation, survival and migration of neural stem cells in vitro and in vivo.

SUMMARY OF THE INVENTION

In one aspect, the invention includes a method of alleviating a symptom of a disorder of the nervous system in a patient comprising administering S1P, LPA or an EDG receptor agonist or a combination thereof to modulate NSC activity in vivo to a patient suffering from the disorder of the nervous system. In this disclosure, a "disorder" shall have the same meaning as a "disease."

In another aspect, the invention includes a method of modulating the activity of a receptor for S1P, LPA, EDG receptor or a combination thereof, on a NSC comprising the step of exposing the cell expressing the receptor to a modulator agent, wherein the exposure induces an NSC to proliferate, differentiate, migrate or survive.

In another aspect, the invention includes a method for stimulating mammalian adult NSC proliferation or neurogenesis comprising the step of contacting a cell population comprising mammalian adult NSC to a agent selected from the group consisting of S1P, LPA or EDG receptor agonist to form a treated NSC, wherein the treated NSC cell shows improved proliferation or neurogenesis compared to untreated cells.

In another aspect, the invention includes a method for stimulating primary adult mammalian NSC to proliferate to form neurospheres comprising contacting the cell with an agent selected from the group consisting of S1P, LPA or EDG receptor agonist to produce a proliferating NSC.

In another aspect, the invention includes a method for inducing the in situ proliferation, differentiation, migration or survival of an NSC located in the neural tissue of a mammal, the method comprising administering a therapeutically effective amount of S1P, LPA or EDG receptor agonist to the neural tissue to induce the proliferation, migration or survival of the cell.

In another aspect, the invention includes a method for accelerating the growth of an NSC in a desired target tissue in a subject, comprising: (a) transfecting the target tissue with an expression vector containing an open reading frame encoding S1P, LPA or EDG receptor gene in a therapeutically effective amount; (b) expressing the open reading frame to produce a protein in the target tissue.

In another aspect, the invention includes a method of enhancing neurogenesis in a patient suffering from a central nervous system disorder comprising the step of infusing S1P, LPA or EDG receptor agonist thereof into the patient.

In another aspect, the invention includes a method of alleviating a symptom of a central nervous system disorder in a patient comprising the step of infusing S1P, LPA or EDG receptor agonist into the patient.

In another aspect, the invention includes a method for producing a cell population enriched for human NSC, comprising: (a) contacting a cell population containing NSC with a reagent that recognizes a determinant on a S1P, LPA or EDG receptor; (b) selecting for cells in which there is contact between the reagent and the determinant on the surface of the cells of step (a) to produce a population highly enriched for central nervous system stem cells.

In another aspect, the invention an in vitro cell culture comprising a cell population generated by the method previously described wherein the cell population is enriched for cells expressing receptors selected from the group consisting of S1P, LPA or EDG receptor.

In another aspect, the invention includes a method for alleviating a symptom of a central nervous system disorder comprising administering the population described above to a mammal in need thereof.

In another aspect, the invention includes a method of reducing a symptom of a central nervous system disorder in a patient comprising the step of administering into the spinal cord of the subject a composition comprising (a) a population of isolated NSCs obtained from fetal or adult tissue; and (b) S1P, LPA or EDG receptor agonist or a combination thereof; whereby the symptom is reduced.

In another aspect, the invention includes a method of reducing a symptom of a central nervous disorder in a patient comprising the steps of: (a) introducing a viral vector into the target cell, wherein the viral vector has at least one insertion site containing a nucleic acid which encodes S1P, LPA or EDG receptor agonist, the nucleic acid gene operably linked to a promoter capable of expression in the host; (b) expressing the nucleic acid to produce a protein in a target cell to reduce the symptom.

In another aspect, the invention includes a method for alleviating a symptom of a disorder of the nervous system in a patient comprising the steps of: (a) providing a population of NSC; (b) suspending the NSC in a solution comprising S1P, LPA or EDG receptor agonist or a combination thereof to generate a cell suspension; (c) delivering the cell suspension to an injection site in the nervous system of the patient to alleviate the symptom.

In another aspect, the invention includes a method for transplanting a population of cells enriched for human NSC, comprising: (a) contacting a population containing NSC with a reagent that recognizes a determinant on a S1P, LPA or EDG receptor; (b) selecting for cells in which there is contact between the reagent and the determinant on the surface of the cells of step (a), to produce a population highly enriched for central nervous system stem cells; and (c) implanting the selected cells of step (b) into a non-human mammal.

In another aspect, the invention includes a method of modulating a S1P, LPA or EDG receptor agonist on the surface of an NSC comprising the step of contacting the cell expressing the receptor to exogenous reagent, antibody, or affibody, wherein the exposure induces the NSC to proliferate, migrate or survive.

In another aspect, the invention includes a method of determining an isolated candidate S1P, LPA or EDG receptor modulator compound for its ability to modulate NSC activity comprising the steps of: (a) administering the isolated candidate compound to a non-human mammal; and (b) determining if the candidate compound has an effect on modulating the NSC activity in the non-human mammal.

One embodiment of the invention is directed to a method of alleviating a symptom of a disorder of the nervous system in a patient. In the method, an S1P receptor agonist, LPA receptor agonist or EDG receptor agonist is administered to a patient suffering from the disorder of the nervous system to modulate NSC activity in vivo in a target tissue. The activity to be modulated may be proliferation, migration or survival. The S1P, LPA or EDG receptor, referred to in any of the methods of the invention, may be used in combination. In this method, the S1P, LPA or EDG receptor (and combination thereof) may be administered in an amount of 0.1 ng/kg/day to 10 mg/kg/day. In a more preferred embodiment, the S1P, LPA or EDG receptor (and combination thereof) may be administered in an amount of to achieve a target tissue concentration of 0.1 nM to 10 µM.

For any reference to EDG receptors in this disclosure, the EDG receptor may be EDG2, EDG3, EDG4 or EDG5. Furthermore, in a preferred embodiment, the EDG receptor, in any reference in this disclosure, is EDG1 or EDG8. For example, a reference to an EDG receptor agonist, would also mean an agonist of EDG1, EDG2, EDG3, EDG4, EDG5 or EDG8.

The target tissue is selected from the group consisting of the ventricular wall, the volume adjacent to the wall of the ventricular system, hippocampus, piriform cortex, alveus, striatum, substantia nigra, retina, nucleus basalis of Meynert, spinal cord, thalamus, hypothalamus piriform cortex and cortex.

The administration methods, in any of the methods of this disclosure, may be by any means. For example, the administration may be by injection. The injection may be given subcutaneously, intraperitoneally, intramusclularly, intracerebroventricularly, intraparenchymally, intrathecally or intracranially. As another example, the administration may be made orally.

The disorder whose symptoms may be treated by the method may be any disease and includes, at least, a neurodegenerative disorders, NSC disorders, neural progenitor disorders, ischemic disorders, neurological traumas, affective disorders, neuropsychiatric disorders, degenerative diseases of the retina, retinal injury/trauma, cognitive performance and learning and memory disorders.

Another embodiment of the invention is directed to a method of modulating the activity of an S1P, LPA, EDG receptor or a combination thereof, on a NSC. The method comprises contacting the cell expressing the receptor to a modulator agent so that the modulator agent induces the NSC to proliferate, differentiate, migrate or survive. The modulator agent may be, for example, an exogenous reagent, an antibody (including monoclonal, polyclonal and engineered antibodies and fragments thereof), an affibody or a combination of these agents. In a preferred embodiment, the modulator agent could be S1P, LPA or a EDG receptor agonist. Also, the modulator agent may be pegylated to enhance its half life after administration. Methods of pegylating proteins and reagents are well known to those of skill in the art and are described, for example, in U.S. Pat. Nos. 5,166,322, 5,766, 897, 6,420,339 and 6,552,170. The NSC of this method may be derived from fetal brain, adult brain, neural cell culture or a neurosphere. For example, the NSC can be derived from tissue enclosed by dura mater, peripheral nerves or ganglia. As a further example, the NSC may be derived from pancreas, skin, muscle, adult bone marrow, liver, umbilical cord tissue and umbilical cord blood.

Another embodiment of the invention is directed to a method for stimulating mammalian adult NSC proliferation or neurogenesis. In the method, a cell population comprising mammalian adult NSC is contacted to an agent such as an S1P receptor agonist, LPA receptor agonist, or EDG receptor agonist to form a treated NSC. The treated NSC will show improved proliferation or neurogenesis compared to untreated cells. The NSC may be derived from lateral ventricle wall of a mammalian brain. As another example, the NSC may be derived from stem cells originating from a tissue such as pancreas, skin, muscle, adult bone marrow, liver, umbilical cord tissue and umbilical cord blood. The NSC, after the application of the method, will show an improved characteristic such as survival, proliferation or migration compared to untreated cells.

Another embodiment of the invention is directed to a method for stimulating primary adult mammalian NSC to proliferate to form neurospheres. In the method, the primary adult mammalian NSC is contacted with an agent. The agent may be an S1P receptor agonist, LPA receptor agonist, or EDG receptor agonist. The contact will produce a proliferating NSC.

Another embodiment of the invention is directed to a method of inducing the in situ proliferation, migration or survival of an NSC located in the neural tissue of a mammal. The method comprise administering a therapeutically effective amount of an S1P receptor agonist, LPA receptor agonist, or EDG receptor agonist to the neural tissue to induce the proliferation, migration or survival of the cell.

Another embodiment of the invention is directed to a method of enhancing neurogenesis in a patient suffering from a central nervous system disorder. The method comprise infusing an S1P receptor agonist, LPA receptor agonist, or EDG receptor agonist thereof into the patient. The infusion may be intraventricular, intravenous, sublingual, subcutaneous or intraarterial infusion.

Another embodiment of the invention is directed to a method of alleviating a symptom of a central nervous system disorder in a patient. In the method, a S1P receptor agonist, LPA receptor agonist, or EDG receptor agonist is infused into the patient.

Another embodiment of the invention is directed to a method for producing a cell population enriched for human NSC. The method comprises contacting a cell population containing NSC with a reagent that recognizes a determinant on an S1P, LPA or EDG receptor; and selecting for cells in which there is contact between the reagent and the determinant on the surface of the cells to produce a population highly enriched for central nervous system stem cells. The reagent may be, for example, a small molecule, a peptide, an antibody and an affibody. The cell population containing NSC may be obtained from neural tissue, such as, for example, from whole mammalian fetal brain or whole mammalian adult brain. The human NSCs may be derived from stem cells originating from a tissue such as pancreas, skin, muscle, adult bone marrow, liver, umbilical cord tissue or umbilical cord blood. An in vitro cell culture derived from the method is also a part of the present invention. In a preferred embodiment, the cell population of the cell culture is enriched for cells expressing receptors selected from the group consisting of an S1P receptor agonist, LPA receptor agonist, or EDG receptor agonist.

Another embodiment of the invention is directed to a method for alleviating a symptom of a central nervous system disorder by administering a cell population of the invention (e.g., a cell culture of the previous paragraph) to a mammal in need thereof.

Another embodiment of the invention is directed to a method of reducing a symptom of a central nervous system disorder in a patient using the step of administering into the spinal cord of the subject a composition comprising a population of isolated NSCs obtained from fetal or adult tissue; and an S1P receptor agonist, LPA receptor agonist, or EDG receptor agonist or a combination thereof so that the symptom is reduced.

Another embodiment of the invention is directed to a method of reducing a symptom of a central nervous disorder in a patient. In the method, a viral vector is introduced into the target cell. The viral vector has at least one insertion site containing a nucleic acid which encodes an S1P receptor agonist, LPA receptor agonist, or EDG receptor agonist, the nucleic acid gene being operably linked to a promoter capable of expression in the host. Then the nucleic acid is expressed to produce a protein in a target cell to reduce the symptom.

Another embodiment of the invention is directed to a method for alleviating a symptom of a disorder of the nervous system in a patient. In the method, a population of NSC is provided and suspended in a solution comprising an S1P receptor agonist, LPA receptor agonist, or EDG receptor agonist or a combination thereof to generate a cell suspension. Then the cell suspension is delivered to an injection site in the nervous system of the patient to alleviate the symptom. Further, in an optional step, a growth may be administered to the injection site for a period of time before the step of delivering the cell suspension. In another optional step, the growth factor may be administered to the injection site a growth factor after the delivering step.

Another embodiment of the invention is directed to a method for transplanting a population of cells enriched for human NSC. First, a population of cells containing NSC is contacted with a reagent that recognizes a determinant on an S1P receptor, LPA receptor or EDG receptor. Then cells in which there is contact between the reagent and the determinant on the surface of the cells is selected to produce a population highly enriched for central nervous system stem cells. Finally, the selected cells are implanted into a non-human mammal.

Another embodiment of the invention is directed to a method of modulating an S1P receptor agonist, LPA receptor agonist or EDG receptor agonist on the surface of an NSC with the step of contacting the cell expressing the receptor to exogenous reagent, antibody, or affibody, so that the exposure induces the NSC to proliferate, migrate or survive. In this method, the NSC is derived from fetal brain, adult brain, neural cell culture or a neurosphere.

Another embodiment of the invention is directed to a method of determining an isolated candidate S1P receptor, LPA receptor aor EDG receptor modulator compound for its ability to modulate NSC activity. In the method a candidate compound is administered to a non-human mammal. Then it is determined if the candidate compound has an effect on modulating the NSC activity in the non-human mammal. The determining step may involve comprises comparing the neurological effects of the non-human mammal with a referenced non-human mammal not administered the candidate compound. The NSC activity may be proliferation, migration or survival. Administration may be by injection and the injection may be given subcutaneously, intraperitoneally, intramusclurly, intracerebroventricularly, intraparenchymally, intrathecally or intracranially. Another preferred method of delivery is administered via peptide fusion or micelle delivery.

Another embodiment of the invention is directed to a method for synergistically stimulating mammalian adult NSC proliferation or neurogenesis. In the method, a cell population comprising mammalian adult neural stem cells is contacted to a growth factor and contacted to an agent selected from the group consisting of an S1P receptor agonist, LPA receptor agonist and EDG receptor agonist. The stimulation is synergistic, which means that the stimulation of mammalian adult NSC proliferation is greater than stimulation by the growth factor or stimulation by the agent alone. It also means that the stimulation of mammalian adult NSC proliferation is greater than the sum of stimulation by growth factor and stimulation by the agent. The preferred growth factor for this method is EGF.

DETAILED DESCRIPTION OF THE INVENTION

Figure 1A:
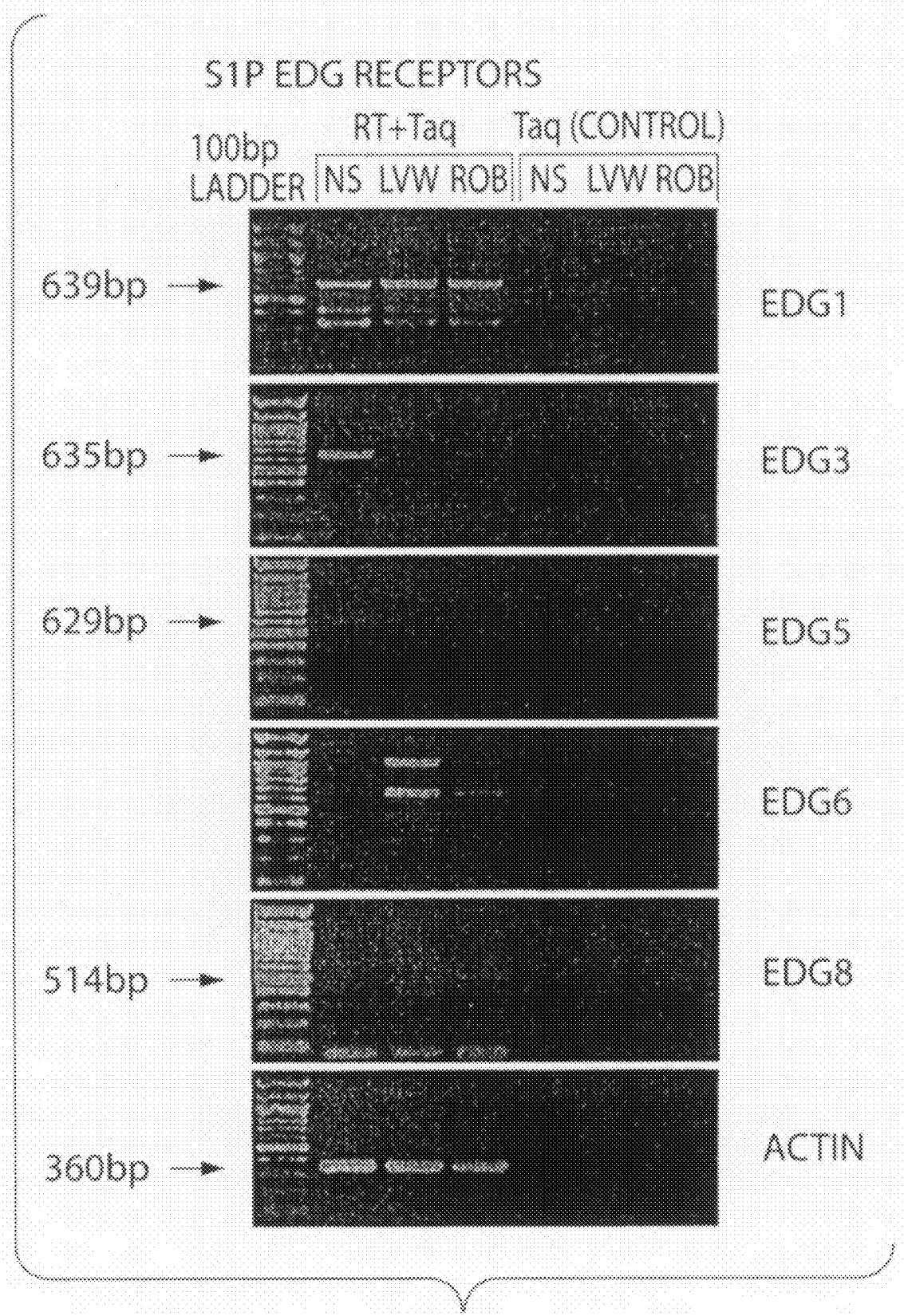
FIG. 1 shows EDG receptor mRNAs are expressed in adult mouse lateral ventricle wall tissue and cultured adult mouse neural stem cells.

It has been discovered that certain reagents are capable of modulating the differentiation, migration, proliferation and survival of neural stem/progenitor cells both in vitro and in vivo. As used herein, the term "modulate" refers to having an affect in such a way as to alter the differentiation, migration, proliferation and survival of neural stem cell (NSC) or neural progenitor cell (NPC) activity. Since undifferentiated, pluripotent stem cells can proliferate in culture for a year or more, the invention described in this disclosure provides an almost limitless supply of neural precursors.

Throughout this disclosure, the term "neural stem cells" (NSCs) includes "neural progenitor cell," "neuronal progenitor cell," "neural precursor cell," and "neuronal precursor cell" (all referred to herein as NPCs). These cells can be identified by their ability to undergo continuous cellular proliferation, to regenerate exact copies of themselves (self-renew), to generate a large number of regional cellular progeny, and to elaborate new cells in response to injury or disease. The term NPCs mean cells that can generate progeny that are either neuronal cells (such as neuronal precursors or mature neurons) or glial cells (such as glial precursors, mature astrocytes, or mature oligodendrocytes). Typically, the cells express some of the phenotypic markers that are characteristic of the neural lineage. They also do not usually produce progeny of other embryonic germ layers when cultured by themselves in vitro unless dedifferentiated or reprogrammed in some fashion. As used herein, the term "neurosphere" refers to the ball of cells consisting of NSCs.

As used herein, the term "reagent" refers to any substance that is chemically and biologically capable of activating a receptor, including peptides, small molecules, antibodies (or fragments thereof), affibodies and any molecule that dimerizes or multimerizes the receptors or replaces the need for activation of the extracellular domains. In one embodiment, the reagent is a small molecule.

As used herein, the term "antibody" or "immunoglobulin" as used in this disclosure refers to both polyclonal and monoclonal antibody and functional derivatives (i.e., engineered antibody) thereof. Antibodies can be whole immunoglobulin of any class, e.g., IgG, IgM, IgA, IgD, IgE, or hybrid antibodies with dual or multiple antigen or epitope specificities, or fragments, e.g., F(ab')2, F(ab)2, Fab', Fab1 and the like, including hybrid fragments. Functional derivatives include engineered antibodies. The ambit of the term deliberately encompasses not only intact immunoglobulin molecules, but also such fragments and derivatives of immunoglobulin molecules (such as single chain Fv constructs, diabodies and fusion constructs) as may be prepared by techniques known in the art, and retaining a desired antibody binding specificity. The term "affibody" (U.S. Pat. No. 5,831,012) refers to highly specific affinity proteins that can be designed to bind to any desired target molecule. These antibody mimics can be manufactured to have the desired properties (specificity and affinity), while also being highly robust to withstand a broad range of analytical conditions, including pH and elevated temperature. The specific binding properties that can be engineered into each capture protein allow it to have very high specificity and the desired affinity for a corresponding target protein. A specific target protein will thus bind only to its corresponding capture protein. The small size (only 58 amino acids), high solubility, ease of further engineering into multifunctional constructs, excellent folding and absence of cysteines, as well as a stable scaffold that can be produced in large quantities using low cost bacterial expression systems, make affibodies superior capture molecules to antibodies or antibody fragments, such as Fab or single chain Fv (scFv) fragments, in a variety of Life Science applications. The term antibodies also encompasses engineered antibodies.

As used herein, the term "engineered antibody" encompasses all biochemically or recombinately produced functional derivatives of antibodies. A protein is a functional derivative of an antibody if it has at least one antigen binding site (ABS) or a complementarity-determining region (CDR) that when combined with other CDR regions (on the same polypeptide chain or on a different polypeptide chain) can form an ABS. The definition of engineered antibody would include, at least, recombinant antibodies, tagged antibodies, labeled antibodies, Fv fragments, Fab fragments, recombinant (as opposed to natural) multimeric antibodies, single chain antibodies, diabodies, triabodies, tetravalent multimers (dimer of diabodies), pentavalent multimers (dimer of diabody and triabody), hexavalent multimers (dimer of triabodies) and other higher multimeric forms of antibodies.

The terms "recombinant nucleic acid" or "recombinantly produced nucleic acid" refer to nucleic acids such as DNA or RNA which has been isolated from its native or endogenous source and modified either chemically or enzymatically by adding, deleting or altering naturally-occurring flanking or internal nucleotides. Flanking nucleotides are those nucleotides which are either upstream or downstream from the described sequence or sub-sequence of nucleotides, while internal nucleotides are those nucleotides which occur within the described sequence or subsequence.

The term "recombinant means" refers to techniques where proteins are isolated, the cDNA sequence coding the protein identified and inserted into an expression vector. The vector is then introduced into a cell and the cell expresses the protein. Recombinant means also encompasses the ligation of coding or promoter DNA from different sources into one vector for expression of a PPC, constitutive expression of a protein, or inducible expression of a protein.

The term "promoter" refers to a DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

The term "enhancer" refers to a promoter element. An enhancer can increase the efficiency with which a particular gene is transcribed into mRNA irrespective of the distance or orientation of the enhancer relative to the start site of transcription.

"Complementary DNA (cDNA)" refers to a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complement.

"Expression" refers to the process by which a polypeptide is produced from a structural gene. The process involves transcription of the gene into mRNA and the translation of such mRNA into polypeptide(s).

"Cloning vector" refers to a DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

"Expression vector" refers to a DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

"Recombinant Host" refers to a prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. The host cell is not limited to a unicellular organism. Multicellular organisms such as mammals, insects, and plants are also contemplated as host cells in the context of this invention. For examples of suitable hosts, see Sambrook et al., MOLECULAR CLONING: A LABORATORY MANUAL, Second Edition, Cold Spring Harbor Laboratory, Cold Spring Harbor, N.Y. (1989).

The term "treating" in its various grammatical forms in relation to the present invention refers to preventing, curing, reversing, attenuating, alleviating, minimizing, suppressing or halting the deleterious effects of a disease state, disease progression, disease causative agent (e.g., bacteria or viruses) or other abnormal condition. Because some of the inventive methods involve the physical removal of the etiological agent, the artisan will recognize that they are equally effective in situations where the inventive compound is administered prior to, or simultaneously with, exposure to the etiological agent (prophylactic treatment) and situations where the inventive compounds are administered after (even well after) exposure to the etiological agent.

The terms "recombinant protein," "recombinantly produced protein" refer to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

According to the specific case, the "therapeutically effective amount" of an agent should be determined as being the amount sufficient to improve the symptoms of the patient in need of treatment or at least to partially arrest the disease and its complications. Amounts effective for such use will depend on the severity of the disease and the general state of the patient's health. Single or multiple administrations may be required depending on the dosage and frequency as required and tolerated by the patient.

As used herein, the term "a method to detect" refers to any assay (including immunoassays and colorimetric assays) known in the art for the measurement of a detectable label. These assays include, at least, assays utilizing biotin and avidin (including streptavidin), ELISA's and immunoprecipitation, immunohistochemical techniques and agglutination assays. A detailed description of these assays is given in WO 96/13590 to Maertens & Stuyver. The term "biological sample" relates to any possible sample taken from an animal (including humans), such as blood (which also encompasses serum and plasma samples), sputum, cerebrospinal fluid, urine, lymph or any possible histological section, and other body fluid. Detection may also include methods of imaging a lesion, such as with immunoscintigraphy, computed tomography (CT), ultrasonography, X-rays, and the like.

The terms "binding specificity," "specifically binds to" or "specifically immunoreactive with," when referring to a protein, antibody, or antibody binding site (ABS) of the invention, refers to a binding reaction which is determinative of the presence of the protein or carbohydrate in the presence of a heterogeneous population of proteins and other biologics. A variety of immunoassay formats may be used to determine binding. For example, solid-phase ELISA immunoassays are routinely used to select antibodies specifically immunoreactive with a protein or carbohydrate. See Harlow & Lane, Antibodies, A Laboratory Manual, Cold Spring Harbor Publication, New York (1988) for a description of immunoassay formats and conditions that can be used to determine specific immunoreactivity.

The terms "isolated" or "substantially purified," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

The terms "nucleic acid encoding" or "nucleic acid sequence encoding" refer to a nucleic acid which directs the expression of a specific protein or peptide. The nucleic acid sequences include both the DNA strand sequence that is transcribed into RNA and the RNA sequence that is translated into protein. The nucleic acid sequences include both full length nucleic acid sequences as well as shorter sequences derived from the full length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex form.

"Pharmaceutical composition" refers to formulations of various preparations. Parenteral formulations are known and are preferred for use in the invention. The formulations containing therapeutically effective amounts of the immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg or more.

EDG Receptors and their Ligands

The lysosphingolipid, sphingosine-1-phosphate (S1P) and the structurally related lipid lysophosphatidic acid (LPA) elicit a wide spectrum of biological responses. The principal effects of LPA and S1P are growth related, including induction of cellular proliferation, alterations in differentiation and survival, and suppression of apoptosis. LPA and S1P also evoke cellular effector functions, which are dependent on cytoskeletal responses such as contraction, secretion, adhesion, and chemotaxis (for reviews see [Goetzl and An, 1998; Pyne and Pyne 2000; (Fukushima and Chun 2001)).

LPA and S1P both may be biosynthesized by cells either de novo through pathways of intermediate lipid metabolism or through stimulus-coupled liberation of the respective precursor glycerophospholipids and sphingolipids and subsequent enzymatic conversions (for review see (Goetzl and An 1998)).

The activation of enzymes involved in the degradation of sphingomyelin to sphingosine (sphingomyelinases, ceramidases) or the phosphorylation of sphingosine to S1P (such as SPHK1 or 2), leading to increased production of S1P, are alternative routes considered to increase the S1P concentration to achieve proliferation or neurogenesis. Likewise, blocking the degradation of S1P thru the S1P phosphatase (SGPP1 or 2) or S1P lyase (SPGL1) will increase the concentration of S1P, and is considered another way to increase signalling thru the EDG receptors. For references, see Spiegel & Kolesnick, Nature (2002) vol 16 no 9, p1596-1602.

Other enzymes that regulate levels of phospholipid of phosphatidic acid are phosphatases which catalyze the dephosphorylation of phosphatidic acid. They have a role in metabolic pathways controlling the synthesis of glycerophospholipids and triacylglycerols, and in receptor-activated signal transduction mediated by phospholipase D. Examples are PPAP2A and PPAP2B, which hydrolyze LPA, ceramide 1-phosphate, or S1P.

S1P and LPA have been proposed to act both as extracellular mediators and as intracellular second messengers (Tigyi, Dyer et al. 1994; Pyne and Pyne 2000). Extracellular effects are mediated via a recently identified family of plasma membrane G protein-coupled receptors (GPCRs), known as the Endothelial Differentiation Gene (EDG) receptors, whereas specific intracellular effects of S1P and LPA are attributable to modifications in the content and/or activity of a major functional protein. Examples are increases in nuclear levels of transcription factors that regulate the serum response element, suppression of death caspase activities in apoptosis, and elevation of membrane content of heparin binding-epidermal growth factor-like growth factor, which serves as an autocrine and juxtacrine stimulus of proliferation (Goetzl and An 1998). Additional receptors that can mediate the effects of S1P or LPA have been described, such as GPR4, GPR68, G2A, GPR45 (psp24), GPR63, GPR3, GPR6, GPR12 (see Uhlenbrock et al., Cellular Signaling 14 (2002) 941-53; Niederberg et al., Cell Signal 2003 April; 15(4):435-46).

Many of the effects of LPA and S1P are abolished by Pertussis Toxin (PTX). PTX specifically inactivates $G_i$ and $G_o$ proteins by ADP-ribosylation of αi subunit, uncoupling the GPCRs from their effector mechanisms. This finding indicated that LPA and S1P could also evoke cellular responses through GPCRs. The first breakthrough in discovery receptors for these ligands came in 1996. Hecht et al. (1996) identified LPA as a ligand for a GPCR they isolated from the ventricular zone of the developing mouse brain (Hecht, Weiner et al. 1996). The cloned and overexpressed vzg-1 gene mediated serum-induced retraction of neurites in cortical neurons, a characteristic response elicited by LPA application in neuroblastoma cells (Jalink, Eichholtz et al. 1993). Vzg-1 was later named EDG2 (Contos, Fukushima et al. 2000) because it was shown to be highly homologous to a family of GPCR orphan receptors. The first member of the family was cloned by Hla and Maciag (1990) as a phorbol ester-induced early response gene in vascular endothelial cells (Hla and Maciag 1990); hence it was named EDG1 for endothelial differentiation gene-1. In 1998 Lee, et al. reported that S1P was an endogenous ligand for EDG1 (Lee, Van Brocklyn et al. 1998). After this report, several groups have identified other members of this family, including the genes for the LPA-specific EDG4 (An, Bleu et al. 1998) and EDG7 (Aoki, Bandoh et al. 2000) receptors and the S1P-specific EDG3 (An, Bleu et al. 1997), EDG5 (An, Bleu et al. 1997), EDG6 (Graler, Bernhardt et al. 1998) and EDG8 (Im, Heise et al. 2000) receptors.

EDG proteins are developmentally regulated and differ in tissue distribution, but couple similarly to multiple types of G-proteins to signal through ras and mitogen-activated protein kinase, rho, phospholipase C, and several protein tyrosine kinases. Furthermore, the EDG receptors are thought to cross-talk with receptor tyrosine kinases to elicit cellular responses. This may allow receptor tyrosine kinase receptors to signal more efficiently and could provide the basis for co-mitogenicity. The best example of this is LPA which stimulate tyrosine phosphorylation and transactivation of the EGF receptor (Zwick, Hackel et al. 1999).

The first suggestion for involvement in the EDG receptors in neurogenesis came with the cloning of EDG2. EDG2 was identified to have enriched expression in proliferating regions of the embryonic cerebral cortex and developing olfactory bulb (Hecht, Weiner et al. 1996; Weiner, Hecht et al. 1998), leading to a proposal for a role of this receptor in cortical neurogenesis. Cell lines derived from this region respond to LPA with morphological changes including neurite retraction/cell rounding, a feature characteristic of cortical neuroblasts during cortical development (Hecht, Weiner et al. 1996). Another prominent feature of ventricular zone neuroblasts, which may be related to LPA signaling, was cell proliferation. Treatment of clusters with LPA for one day resulted in the increase in the proliferative population, as determined by 5-bromo-2'-deoxyuridine-5'-monophosphate incorporation. This increase was inhibited by the pretreatment with PTX suggesting the involvement of $G_{i/o}$ pathway (Contos, Fukushima et al. 2000).

The effects of S1P and its receptors on cellular function in the brain are less well characterised than for LPA. However, recent evidence has implicated a role for S1P in astrocyte proliferation (Pebay, Toutant et al. 2001). S1P evoked ERK phosphorylation and subsequent DNA synthesis when applied to astrocytes. The stimulatory effect of S1P on astrocyte proliferation was totally blocked by PTX, indicating that these effects are mediated through GPCRs coupled to Gi/Go proteins, a criteria fulfilled by the S1P EDG receptors. Additional neurobiological effects of S1P include morphological changes, such as neurite retraction (Postma, Jalink et al. 1996) and neural differentiation (Rius, Edsall et al. 1997).

In a recent paper the expression pattern of LPA and S1P EDG receptors has been analysed and compared in the embryonic brain by in situ hybridization (McGiffert, Contos et al. 2002). Their data demonstrated prominent expression of EDG1 adjacent to the lateral ventricle in a manner both spacially and temporarily coincident with neurogenesis. EDG1 expressing cells were found to label positively for BrdU, a thymidine analog incorporated into dividing cells upon application, in the ventricular zone of the cerebral cortex and ganglionic eminence and the hippocampal primordial, indicating that EDG1 expression is coincident with proliferating cells in the developing brain. Expression of EDG1, EDG3 and EDG5 was also observed to exist in a punctuate pattern, colocalising with vascular endothelial markers. These results suggest that EDG1 influences neurogenesis and EDG1, EDG3 and EDG5 in angiogenesis in the developing brain.

Evidence has also come to light on expression of the LPA receptors, EDG2, EDG4 and EDG7 in hepatic oval stem/progenitor cells, suggesting that the expression of these receptors and their regulation may play an important role in the mechanism of activation of hepatic oval stem/progenitor cells (Sautin, Jorgensen et al. 2002). Furthermore, the investigators suggest that LPA and its analogs may represent important endogenous mediators, regulating functions such as survival, motility, proliferation and differentiation of hepatocyte progenitors in liver.

Neurogenesis has recently been observed in the piriform cortex in the adult monkey (Bernier, Bedard et al. 2002), confirming evidence from a study performed on rats (Bayer 1986). These investigations suggest that neurogenesis may be more widespread than has first thought.

Production of Reagents

Reagents for treatment of patients are recombinantly produced, purified and formulated according to well-known methods.

Reagents of the invention and individual moieties or analogs and derivatives thereof, can be chemically synthesized. A variety of protein synthesis methods are common in the art, including synthesis using a peptide synthesizer. See, e.g., *Peptide Chemistry, A Practical Textbook*, Bodasnsky, Ed. Springer-Verlag, 1988; Merrifield, Science 232: 241-247 (1986); Barany, et al, Intl. J. Peptide Protein Res. 30: 705-739 (1987); Kent, Ann. Rev. Biochem. 57:957-989 (1988), and Kaiser, et al, Science 243: 187-198 (1989). The peptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of peptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, e.g., receptor binding, functional potency or duration of action. See, e.g., Doherty, et al., 1993. J. Med. Chem. 36: 2585-2594; Kirby, et al., 1993, J. Med. Chem. 36:3802-3808; Morita, et al., 1994, FEBS Lett. 353: 84-88; Wang, et al., 1993 Int. J. Pept. Protein Res. 42: 392-399; Fauchere and Thiunieau, 1992. Adv. Drug Res. 23: 127-159.

Introduction of covalent cross-links into a peptide sequence can conformationally and topographically constrain the peptide backbone. This strategy can be used to develop peptide analogs of reagents with increased potency, selectivity and stability. A number of other methods have been used successfully to introduce conformational constraints into peptide sequences in order to improve their potency, receptor selectivity and biological half-life. These include the use of (i) $C_\alpha$-methylamino acids (see, e.g., Rose, et al., Adv. Protein Chem. 37: 1-109 (1985); Prasad and Balaram, *CRC Crit. Rev. Biochem.,* 16: 307-348 (1984)); (ii) $N_\alpha$-methylamino acids (see, e.g., Aubry, et al., Int. J. Pept. Protein Res., 18: 195-202 (1981); Manavalan and Momany, Biopolymers, 19: 1943-1973 (1980)); and (iii) $\alpha,\beta$-unsaturated amino acids (see, e.g., Bach and Gierasch, Biopolymers, 25: 5175-S192 (1986); Singh, et al., Biopolymers, 26: 819-829 (1987)). These and many other amino acid analogs are commercially available, or can be easily prepared. Additionally, replacement of the C-terminal acid with an amide can be used to enhance the solubility and clearance of a peptide.

Alternatively, a reagent may be obtained by methods well-known in the art for recombinant peptide expression and purification. A DNA molecule encoding the protein reagent can be generated. The DNA sequence is known or can be deduced from the protein sequence based on known codon usage. See, e.g., Old and Primrose, *Principles of Gene Manipulation* $3^{rd}$ ed., Blackwell Scientific Publications, 1985; Wada et al., Nucleic Acids Res. 20: 2111-2118 (1992). Preferably, the DNA molecule includes additional sequence, e.g., recognition sites for restriction enzymes which facilitate its cloning into a suitable cloning vector, such as a plasmid. Nucleic acids may be DNA, RNA, or a combination thereof. Nucleic acids encoding the reagent may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like). Nucleic acids can also be generated by chemical synthesis.

Any of the methodologies known within the relevant art regarding the insertion of nucleic acid fragments into a vector may be used to construct expression vectors that contain a chimeric gene comprised of the appropriate transcriptional/ translational control signals and reagent-coding sequences. Promoter/enhancer sequences within expression vectors may use plant, animal, insect, or fungus regulatory sequences, as provided in the invention.

A host cell can be any prokaryotic or eukaryotic cell. For example, the peptide can be expressed in bacterial cells such as *E. coli*, insect cells, fungi or mammalian cells (such as Chinese hamster ovary cells (CHO) or COS cells). Other suitable host cells are known to those skilled in the art. In one embodiment, a nucleic acid encoding a reagent is expressed in mammalian cells using a mammalian expression vector. Examples of mammalian expression vectors include pCDM8 (Seed (1987) Nature 329:840) and pMT2PC (Kaufman et al. (1987) EMBO J 6: 187-195).

The host cells, can be used to produce (e.g., overexpress) peptide in culture. Accordingly, the invention further provides methods for producing the peptide using the host cells of the invention. In one embodiment, the method comprises culturing the host cell of invention (into which a recombinant expression vector encoding the peptide has been introduced) in a suitable medium such that peptide is produced. The method further involves isolating peptide from the medium or the host cell. Ausubel et al., (Eds). In: *Current Protocols in Molecular Biology*. J. Wiley and Sons, New York, N.Y. 1998.

An "isolated" or "purified" recombinant peptide or biologically active portion thereof is substantially free of cellular material or other contaminating proteins from the cell or tissue source from which the peptide of interest is derived. The language "substantially free of cellular material" includes preparations in which the peptide is separated from cellular components of the cells from which it is isolated or recombinantly produced. In one embodiment, the language "substantially free of cellular material" includes preparations of peptide having less than about 30% (by dry weight) of peptide other than the desired peptide (also referred to herein as a "contaminating protein"), more preferably less than about 20% of contaminating protein, still more preferably less than about 10% of contaminating protein, and most preferably less than about 5% contaminating protein. When the peptide or biologically active portion thereof is recombinantly produced, it is also preferably substantially free of culture medium, e.g., culture medium represents less than about 20%, more preferably less than about 10%, and most preferably less than about 5% of the volume of the peptide preparation.

The invention also pertains to variants of a reagent that function as either agonists (mimetics) or as antagonists. Variants of a reagent can be generated by mutagenesis, e.g., discrete point mutations. An agonist of a reagent can retain substantially the same, or a subset of, the biological activities of the naturally occurring form of the reagent. An antagonist of the reagent can inhibit one or more of the activities of the naturally occurring form of the reagent by, for example, competitively binding to the receptor. Thus, specific biological effects can be elicited by treatment with a variant with a limited function. In one embodiment, treatment of a subject with a variant having a subset of the biological activities of the naturally occurring form of the reagent has fewer side effects in a subject relative to treatment with the naturally occurring form of the reagent.

Preferably, the analog, variant, or derivative reagent is functionally active. As utilized herein, the term "functionally active" refers to species displaying one or more known functional attributes of a full-length reagent. "Variant" refers to a reagent differing from naturally occurring reagent, but retaining essential properties thereof. Generally, variants are overall closely similar, and in many regions, identical to the naturally occurring reagent.

Variants of the reagent that function as either agonists (mimetics) or as antagonists can be identified by screening combinatorial libraries of mutants of the reagent for peptide agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential sequences is expressible as individual peptides, or alternatively, as a set of larger fusion proteins (e.g., for phage display) containing the set of sequences therein. There are a variety of methods which can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential sequences. Methods for synthesizing degenerate oligonucleotides are known in the art (see, e.g., Narang (1983) Tetrahedron 39:3; Itakura et al. (1984) Annu Rev Biochem 53:323; Itakura et al. (1984) Science 198:1056; Ike et al. (1983) Nucl. Acids Res. 11:477.

Derivatives and analogs of the reagent or individual moieties can be produced by various methods known within the art. For example, the polypeptide sequences may be modified by any number of methods known within the art. See e.g., Sambrook, et al., 1990. *Molecular Cloning: A Laboratory Manual, 2nd ed.*, (Cold Spring Harbor Laboratory Press; Cold Spring Harbor, N.Y.). Modifications include: glycosylation, acetylation, phosphorylation, amidation, derivatization by known protecting/blocking groups, linkage to an antibody molecule or other cellular reagent, and the like. Any of the numerous chemical modification methodologies known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Derivatives and analogs may be full length or other than full length, if said derivative or analog contains a modified nucleic acid or amino acid, as described infra. Derivatives or analogs of the reagent include, but are not limited to, molecules comprising regions that are substantially homologous in various embodiments, of at least 30%, 40%, 50%, 60%, 70%, 80%, 90% or preferably 95% amino acid identity when: (i) compared to an amino acid sequence of identical size; (ii) compared to an aligned sequence in that the alignment is done by a computer homology program known within the art (e.g., Wisconsin GCG software) or (iii) the encoding nucleic acid is capable of hybridizing to a sequence encoding the aforementioned peptides under stringent (preferred), moderately stringent, or non-stringent conditions. See, e.g., Ausubel, et al., *Current Protocols in Molecular Biology*, John Wiley and Sons, New York, N.Y., 1993.

Derivatives of the reagent may be produced by alteration of their sequences by substitutions, additions or deletions that result in functionally-equivalent molecules. One or more amino acid residues within the reagent may be substituted by another amino acid of a similar polarity and net charge, thus resulting in a silent alteration. Conservative substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

The reagent can be administered locally to any loci implicated in the CNS disorder pathology, e.g. any loci deficient in neural cells as a cause of the disease. For example, the reagent can be administered locally to the ventricle of the brain, substantia nigra, striatum, locus ceruleous, nucleus basalis of Meynert, pedunculopontine nucleus, cerebral cortex, spinal cord and retina.

Neural stem cells and their progeny can be induced to proliferate, differentiate, survive or migrate in vivo by administering to the host a reagent, alone or in combination with other agents, or by administering a pharmaceutical composition containing the reagent that will induce proliferation and differentiation of the cells. Pharmaceutical compositions include any substance that blocks the inhibitory influence and/or stimulates neural stem cells and stem cell progeny to proliferate, differentiate, migrate and/or survive. Such in vivo manipulation and modification of these cells allows cells lost, due to injury or disease, to be endogenously replaced, thus obviating the need for transplanting foreign cells into a patient.

Antibodies

Included in the invention are antibodies to be used as reagents. The term "antibody" as used herein refers to immunoglobulin molecules and immunologically active portions of immunoglobulin (Ig) molecules, e.g., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of an EDG receptor that is located on the surface of the protein, e.g., a hydrophilic region. A hydrophobicity analysis of the human those protein sequences will indicate which regions of the polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each incorporated herein by reference in their entirety. Antibodies that are specific for one or more domains within an antigenic protein, or derivatives, fragments, analogs or homologs thereof, are also provided herein.

The term "epitope" includes any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. A receptor polypeptide or a fragment thereof comprises at least one antigenic epitope.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal Antibodies

The term "monoclonal antibody" (MAb) or "monoclonal antibody composition," as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin and contain minimal sequence derived from a non-human immunoglobulin. Humanization can be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al, (Nature Biotechnology 14, 845-51 (1996)); Neuberger (Nature Biotechnology 14, 826 (1996)); and Lonberg and Huszar (Intern. Rev. Immunol. 13 65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

FAB Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an $F_{(ab)2}$ fragment produced by pepsin digestion of an antibody molecule; (ii) an $F_{ab}$ fragment generated by reducing the disulfide bridges of an $F_{(ab)2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA or TETA. Another bispecific antibody of interest binds the protein antigen described herein and further binds tissue factor (TF).

Immunoliposomes

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Antibody Therapeutics

Antibodies of the invention, including polyclonal, monoclonal, humanized and fully human antibodies, may be used as therapeutic agents such as one of this invention. Such agents will generally be employed to treat or prevent a disease or pathology, specifically neurological disease, in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous S1P or LPA ligand to which it naturally binds. In this case, the antibody binds to the target and masks a binding site of the naturally occurring ligand, wherein the ligand serves as an effector molecule. Thus, the receptor mediates a signal transduction pathway for which ligand is responsible.

Alternatively, the effect may be one in which the antibody elicits a physiological result by virtue of binding to an effector binding site on the target molecule. In this case the target, an EDG receptor having an endogenous ligand which needs to be modulated, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen and the rate at which an administered antibody is depleted from the free volume of the subject to which it is administered.

Diseases and Disorders

Diseases and disorders that are characterized by altered (relative to a subject not suffering from the disorder) levels or biological activity may be treated with therapeutics that antagonize (e.g., reduce or inhibit) or activate S1P or LPA activity. Therapeutics that antagonize activity may be administered in a therapeutic or prophylactic manner. Therapeutics that may be utilized include, but are not limited to: (i) an aforementioned peptide, analog, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (e.g., due to a heterologous insertion within the coding sequences of coding sequences to an aforementioned peptide) that are utilized to "knockout" endogenous function of an aforementioned peptide by homologous recombination (see, e.g., Capecchi, 1989. Science 244: 1288-1292); or (v) modulators (e.g., inhibitors, agonists and antagonists, including additional peptide mimetic of the invention or antibodies specific to a peptide of the invention) that alter the interaction between an aforementioned peptide and its binding partner.

Disorders that are characterized by altered (relative to a subject not suffering from the disease or disorder) levels or biological activity may be treated with therapeutics that increase (e.g., are agonists to) activity. In a preferred embodiment, the diseases to be treated include Alzheimer's disease, stroke, Parkinson's disease. Therapeutics that upregulate activity may be administered in a therapeutic or prophylactic manner. Therapeutics that may be utilized include, but are not limited to, an aforementioned peptide, analog, derivatives, fragments or homologs thereof; or an agonist that increases bioavailability.

Increased or decreased levels can be detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Therapeutic Methods

Another aspect of the invention pertains to methods of modulating S1P or LPA levels or activity for therapeutic purposes. In one embodiment, the modulatory method of the invention involves contacting a cell with an agent that modulates one or more of the activities of S1P or LPA. An agent that modulates this activity can be an agent as described herein, such as a naturally-occurring cognate ligand of an EDG receptor, or other small molecule. In one embodiment, the agent stimulates the activity of the S1P or LPA signaling pathway. Examples of such stimulatory agents include active S1P or LPA or other ligands of the EDG receptors. These modulatory methods can be performed in vitro (e.g., by culturing the cell with the agent) or, alternatively, in vivo (e.g., by administering the agent to a subject). As such, the invention provides methods of treating an individual afflicted with a disorder, specifically a neurological disorder. In one embodiment, the method involves administering a reagent (e.g., an reagent identified by a screening assay described herein), or combination of reagents that modulate (e.g., up-regulates or down-regulates) S1P or LPA expression or activity. In another embodiment, the method involves administering S1P or LPA as therapy to modulate proliferation, differentiation, migration and/or survival of NSCs/NPCs.

Stimulation of S1P or LPA activity is desirable in situations in which S1P or LPA are abnormally downregulated and/or in which increased S1P or LPA levels or activity is likely to have a beneficial effect. One example of such a situation is where a subject has a disorder characterized by aberrant cell proliferation and/or differentiation (e.g., Parkinson's disease and Alzheimer's disease).

Determination of the Biological Effect of the Therapeutic

In various embodiments of the invention, suitable in vitro or in vivo assays are performed to determine the effect of a specific therapeutic and whether its administration is indicated for treatment of the affected tissue.

In various specific embodiments, in vitro assays may be performed with representative stem cells or newly differentiated cells involved in the patient's disorder, to determine if a given therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Pharmaceutical Compositions

The invention provides methods of influencing central nervous system cells to produce progeny that can replace damaged or missing neurons in the central nervous system or other central nervous system cell types by exposing a patient, suffering from a neurological disorder, to a reagent (e.g. S1P, LPA) in a suitable formulation through a suitable route of administration, that modulates NSC or NPC activity in vivo. In all embodiment of the inventions, the reference to disorder of the nervous system may include any disorder and, for example, at least the following disorders: neurodegenerative disorders, neural stem cell disorders, neural progenitor disorders, ischemic disorders, neurological traumas, affective disorders, neuropsychiatric disorders, degenerative diseases of the retina, retinal injury/trauma and learning and memory disorders. In one embodiment of the invention, the disorder of the nervous system is selected from the group consisting of Parkinson's disease and Parkinsonian disorders, Huntington's disease, Alzheimer's disease, Amyotrophic Lateral Sclerosis, spinal ischemia, ischemic stroke, spinal cord injury and cancer-related brain/spinal cord injury. In a further embodiment of the invention, the disorder of the nervous system is selected from the group consisting of schizophrenia and other psychoses, lissencephaly syndrome, depression, bipolar depression/disorder, anxiety syndromes/disorders, phobias, stress and related syndromes, cognitive function disorders, aggression, drug and alcohol abuse, obsessive compulsive behaviour syndromes, seasonal mood disorder, borderline personality disorder, cerebral palsy, life style drug, multi-infarct dementia, Lewy body dementia, age related/geriatric dementia, epilepsy and injury related to epilepsy, temporal lobe epilepsy, spinal cord injury, brain injury, brain surgery, trauma related brain/spinal cord injury, anti-cancer treatment related brain/spinal cord tissue injury, infection and inflammation related brain/spinal cord injury, environmental toxin related brain/spinal cord injury, multiple sclerosis, autism, attention deficit disorders, narcolepsy, sleep disorders, and disorders of cognitive performance or memory.

This invention provides a method of treating a neurological disorder comprising administering a reagent that modulates neural stem cell or neural progenitor cell activity in vivo to a mammal. The term "mammal" refers to any mammal classified as a mammal, including humans, cows, horses, dogs, sheep and cats. In one embodiment, the mammal is a human.

The invention provides a regenerative cure for neurodegenerative diseases by stimulating ependymal cells and subventricular zone cells to proliferate, migrate, differentiate and survive into the desired neural phenotype targeting loci where cells are damaged or missing. In vivo stimulation of ependymal stem cells is accomplished by locally administering a reagent to the cells in an appropriate formulation. By increasing neurogenesis, damaged or missing neurons can be replaced in order to enhance brain function in diseased states.

A pharmaceutical composition useful as a therapeutic agent for the treatment of central nervous system disorders is provided. For example, the composition includes a reagent of the invention, which can be administered alone or in combination with the systemic or local co-administration of one or more additional agents. Such agents include preservatives, ventricle wall permeability increasing factors, stem cell mitogens, survival factors, glial lineage preventing agents, anti-apoptotic agents, anti-stress medications, neuroprotectants, and anti-pyrogenics. The pharmaceutical composition preferentially treats CNS diseases by stimulating cells (e.g., ependymal cells and subventricular zone cells) to proliferate, migrate and differentiate into the desired neural phenotype, targeting loci where cells are damaged or missing.

A method for treating a subject suffering from a CNS disorder is also provided. This method comprises administering to the subject an effective amount of a pharmaceutical composition containing a reagent (1) alone in a dosage range of 0.001 ng/kg/day to 10 mg/kg/day, preferably in a dosage range of 0.01 ng/kg/day to 5 mg/kg/day, more preferably in a dosage range of 0.1 ng/kg/day to 1 mg/kg/day, most preferably in a dosage range of 100 ng/kg/day to 1 mg/kg/day, (2) in a combination with a ventricle wall permeability increasing factor, or (3) in combination with a locally or systemically co-administered agent.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimeric peptide) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Nucleic acid molecules encoding a proteinaceous agent can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

In another embodiments, the reagent is administered in a composition comprising at least 90% pure reagent. The reagent can be, for example, S1P or LPA.

Preferably the reagent is formulated in a medium providing maximum stability and the least formulation-related side-effects. In addition to the reagent, the composition of the invention will typically include one or more protein carrier, buffer, isotonic salt and stabilizer.

In some instances, the reagent can be administered by a surgical procedure implanting a catheter coupled to a pump device. The pump device can also be implanted or be extracorporally positioned. Administration of the reagent can be in intermittent pulses or as a continuous infusion. Devices for injection to discrete areas of the brain are known in the art (see, e.g., U.S. Pat. Nos. 6,042,579; 5,832,932; and 4,692, 147).

Reagents containing compositions can be administered in any conventional form for administration of a protein. A reagent can be administered in any manner known in the art in which it may either pass through or by-pass the blood-brain barrier. Methods for allowing factors to pass through the blood-brain barrier include minimizing the size of the factor, providing hydrophobic factors which may pass through more easily, conjugating the protein reagent or other agent to a carrier molecule that has a substantial permeability coefficient across the blood brain barrier (see, e.g., U.S. Pat. No. 5,670,477).

Reagents, derivatives, and co-administered agents can be incorporated into pharmaceutical compositions suitable for administration. Such compositions typically comprise the agent and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the agents to affect solubility or clearance of the peptide. Peptidic molecules may also be synthesized with D-amino acids to increase resistance to enzymatic degradation. In some cases, the composition can be co-administered with one or more solubilizing agents, preservatives, and permeation enhancing agents. Examples of pharmaceutically acceptable carriers include lactose, glucose, sucrose, sorbitol, mannitol, corn starch, crystalline cellulose, gum arabic, calcium phosphate, alginates, calcium silicate, microcrystalline cellulose, polyvinyl pyrrolidone, tragacanth gum, gelatin, syrum, methyl cellulose, carboxymethyl cellulose, methylhydroxybenzoic acid esters, propylhydroxybenzoic acid esters, talc, magnesium stearates, inert polymers, water and mineral oils.

For example, the composition can include a preservative or a carrier such as proteins, carbohydrates, and compounds to increase the density of the pharmaceutical composition. The composition can also include isotonic salts and redox-control agents.

In some embodiments, the composition administered includes the reagent and one or more agents that increase the permeability of the ventricle wall, e.g. "ventricle wall permeability enhancers." Such a composition can help an injected composition penetrate deeper than the ventricle wall. Examples of suitable ventricle wall permeability enhancers include, for example, liposomes, VEGF (vascular endothelial growth factor), IL-s, TNFα, polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid and derivatives, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, dodecyltrimethylammonium bromide, and dimethyl-β-cyclodextrin or other cyclodextrins.

Drug Screening

The invention also provides a method of using the receptors or receptor/reagent complexes for analyzing or purifying certain stem or progenitor cell populations, using e.g. antibodies, against the receptors or receptor/reagent complexes.

In another aspect, the invention provides a method for screening for reagents that influence stem and progenitor cells. In some applications, neural cells (undifferentiated or differentiated) are used to screen factors that promote maturation into neural cells, or promote proliferation and maintenance of such cells in long-term culture. For example, candidate reagents are tested by adding them to cells in culture at varying dosages, and then determining any changes that result, according to desirable criteria for further culture and use of the cells. Physical characteristics of the cells can be analyzed by observing cell and neurite growth with microscopy. The induction of expression of increased levels of proliferation, differentiation and migration can be analyzed with any technique known in the art which can identify proliferation and differentiation. Such techniques include RT-PCR, in situ hybridization, and ELISA.

In one aspect, novel receptor/reagents in undifferentiated neurospheres was examined using RT-PCR techniques. In particular, genes that are up-regulated in these undifferentiated neurospheres were identified. As used herein, the term "up-regulation" refers to a process that increases reagent/ receptor interactions due to an increase in the number of available receptors. The presence of these genes suggests a potential role in the mediation of signal transduction pathways in the regulation of NSC/NPC function. Furthermore, by knowing the levels of expression of the receptors or their various reagents, it is possible to diagnose disease or determine the role of stem and progenitor cells in the disease. By analyzing the genetic or amino-acid sequence variations in these genes or gene products, it is possible to diagnose or predict the development of certain diseases. Such analysis will provide the necessary information to determine the usefulness of using stem or progenitor cell based treatments for disease.

In another aspect, in situ hybridization is performed on adult mouse brain sections to determine which cells in the adult brain express these signaling pathways. This data is helpful in determining treatment options for various neurological diseases.

To determine the effect of a potential reagent on neural cells, a culture of NSCs/NPCs derived from multipotent stem cells can be obtained from normal neural tissue or, alternatively, from a host afflicted with a CNS disorder. The choice of culture will depend upon the particular agent being tested and the effects one wishes to achieve. Once the cells are obtained from the desired donor tissue, they are proliferated in vitro in the presence of a proliferation-inducing reagent.

The ability of various biological agents to increase, decrease or modify in some other way the number and nature of the stem cell progeny proliferated in the presence of the proliferative factor can be screened on cells proliferated by the methods previously discussed. For example, it is possible to screen for reagents that increase or decrease the proliferative ability of NSCs/NPCs which would be useful for generating large numbers of cells for transplantable purposes. In these studies precursor cells are plated in the presence of the reagent in question and assayed for the degree of proliferation and survival or progenitor cells and their progeny can be determined. It is possible to screen neural cells which have already been induced to differentiate prior to the screening. It is also possible to determine the effects of the reagent on the differentiation process by applying them to precursors cells prior to differentiation. Generally, the reagent will be solubilized and added to the culture medium at varying concentrations to determine the effect of the agent at each dose. The culture medium may be replenished with the reagent every couple of days in amounts so as to keep the concentration of the reagent somewhat constant.

Changes in proliferation are observed by an increase or decrease in the number of neurospheres that form and/or an increase or decrease in the size of the neurospheres, which is a reflection of the rate of proliferation and is determined by the numbers of precursor cells per neurosphere.

Using these screening methods, it is possible to screen for potential drug side-effects on prenatal and postnatal CNS cells by testing for the effects of the biological agents on stem cell and progenitor cell proliferation and on progenitor cell differentiation or the survival and function of differentiated CNS cells.

Other screening applications of this invention relate to the testing of pharmaceutical compounds for their effect on neural tissue. Screening may be done either because the compound is designed to have a pharmacological effect on neural cells, or because a compound designed to have effects elsewhere may have unintended side effects on the nervous system. The screening can be conducted using any of the neural precursor cells or terminally differentiated cells of the invention.

Effect of cell function can be assessed using any standard assay to observe phenotype or activity of neural cells, such as receptor binding, proliferation, differentiation, survival-either in cell culture or in an appropriate model.

Therapeutic Uses

The fact that neural stem cells are located in the tissues lining ventricles of mature brains offers several advantages for the modification and manipulation of these cells in vivo and the ultimate treatment of various neurological diseases, disorders, and injury that affect different regions of the CNS. Therapy for these diseases can be tailored accordingly so that stem cells surrounding ventricles near the affected region would be manipulated or modified in vivo using the methods described herein. The ventricular system is found in nearly all brain regions and thus allows easier access to the affected areas. In order to modify the stem cells in vivo by exposing them to a composition comprising a reagent, it is relatively easy to implant a device that administers the composition to the ventricle and thus, to the neural stem cells. For example, a cannula attached to an osmotic pump may be used to deliver the composition. Alternatively, the composition may be injected directly into the ventricles. The neural stem cell progeny can migrate into regions that have been damaged as a result of injury or disease. Furthermore, the close proximity of the ventricles to many brain regions would allow for the diffusion of a secreted neurological agent by the stem cells or their progeny.

In an additional embodiment, a reagent of the invention is administered locally, as described above, in combination with an agent administered locally or systemically. Such agents include, for example, one or more stem cell mitogens, survival factors, glial-lineage preventing agents, anti-apoptotic agents, anti-stress medications, neuroprotectants, and anti-pyrogenics, or any combination thereof.

The agent is administered systemically before, during, or after administration of the reagent of the invention. The locally administered agent can be administered before, during, or after the reagent administration.

For treatment of Huntington's Disease, Alzheimer's Disease, Parkinson's Disease, and other neurological disorders affecting primarily the forebrain, a reagent alone or with an additional agent or agents is delivered to the ventricles of the forebrain to affect in vivo modification or manipulation of the stem cells. For example, Parkinson's Disease is the result of low levels of dopamine in the brain, particularly the striatum. It is therefore advantageous to induce a patient's own quiescent stem cells to begin to divide in vivo and to induce the progeny of these cells to differentiate into dopaminergic cells in the affected region of the striatum, thus locally raising the levels of dopamine.

Normally the cell bodies of dopaminergic neurons are located in the substantia nigra and adjacent regions of the mesencephalon, with the axons projecting to the striatum. The methods and compositions of the invention provide an alternative to the use of drugs and the controversial use of large quantities of embryonic tissue for treatment of Parkinson's disease. Dopamine cells can be generated in the striatum by the administration of a composition comprising a reagent of the invention to the lateral ventricle.

For the treatment of MS and other demyelinating or hypomyelinating disorders, and for the treatment of Amyotrophic Lateral Sclerosis or other motor neuron diseases, a reagent of the invention, alone or with an additional agent or agents is delivered to the central canal.

In addition to treating CNS tissue immediately surrounding a ventricle, a reagent of the invention, alone or with an additional agent or agents can be administered to the lumbar cistern for circulation throughout the CNS.

In other aspects, neuroprotectants can also be co-administered systemically or locally before, during and/or after infusion of a regent of the invention. Neuroprotectants include antioxidants (agents with reducing activity, e.g., selenium, vitamin E, vitamin C, glutathione, cysteine, flavinoids, quinolines, enzymes with reducing activity, etc), Ca-channel modulators, Na-channel modulators, glutamate receptor modulators, serotonin receptor agonists, phospholipids, unsaturated- and polyunsaturated fatty acids, estrogens and selective estrogen receptor modulators (SERMS), progestins, thyroid hormone and thyroid hormone-mimicking compounds, cyclosporin A and derivatives, thalidomide and derivatives, methylxanthines, MAO inhibitors; serotonin-, noradrenaline and dopamine uptake blockers; dopamine agonists, L-DOPA, nicotine and derivatives, and NO synthase modulators.

Certain reagents of the invention may be pyrogenic following IV injection (in rats; Am. J. Physiol. Regul. Integr. Comp. Physiol. 2000 278:R1275-81). Thus, in some aspects of the invention, antipyrogenic agents like cox2 inhibitors, indomethacin, salisylic acid derivatives and other general anti-inflammatory/anti-pyrogenic compounds can be systemically or locally administered before, during and/or after administration of the reagent of the invention.

In another aspect of the invention, anti-apoptotic agents including caspase inhibitors and agents useful for antisense-modulation of apoptotic enzymes and factors can be administered before, during, or after administration of the reagent of the invention.

Stress syndromes lower neurogenesis, therefore in some aspects, it may be desirable to treat a subject with anti-stress medications such as, e.g., anti-glucocorticoids (e.g., RU486) and beta-blockers, administered systemically or locally before, during and/or after infusion of the reagent of the invention.

Methods for preparing the reagent dosage forms are known, or will be apparent, to those skilled in this art.

The amount of reagent to be administered will depend upon the exact size and condition of the patient, but will be from 0.5 ng/kg/day to 10 mg/kg/day in a volume of 0.001 to 10 ml.

The duration of treatment and time period of administration of reagent will also vary according to the size and condition of the patient, the severity of the illness and the specific composition and method being used.

The effectiveness of each of the foregoing methods for treating a patient with a CNS disorder is assessed by any known standardized test for evaluating the disease.

EXAMPLES

Example 1

Expression of EDG Receptor Genes in Adult Mouse NSC and Lateral Ventricle Wall Tissue Methods Mouse & Human Cultures Mouse Neurosphere Cultures The anterior lateral wall of the lateral ventricle of 5-6 week old mice was enzymatically dissociated in 0.8 mg/ml hyaluronidase and 0.5 mg/ml trypsin in DMEM containing 4.5 mg/ml glucose and 80 units/ml DNase at 37° C. for 20 min. The cells were gently triturated and mixed with three volumes of Neurosphere medium (DMEM/F12, B27 supplement, 12.5 mM HEPES pH7.4) containing 20 ng/ml EGF (unless otherwise stated), 100 units/ml penicillin and 100 μg/ml streptomycin. After passing through a 70 μm strainer, the cells were pelleted at 160×g for 5 min. The supernatant was subsequently removed and the cells resuspended in Neurosphere medium supplemented as above, plated out in culture dishes and incubated at 37° C. Neurospheres were ready to be split approximately 7 days after plating.

To split neurosphere cultures, neurospheres were collected by centrifugation at 160×g for 5 min. The neurospheres were resuspended in 0.5 ml Trypsin/EDTA in HBSS (1×), incubated at 37° C. for 2 min and triturated gently to aid dissociation. Following a further 3 min incubation at 37° C. and trituration, 3 volumes of ice cold NSPH-media-EGF were added to stop further trypsin activity. The cells were pelleted at 220×g for 4 min, resuspended in fresh Neurosphere medium supplemented with 20 ng/ml EGF and 1 nM bFGF plated out and incubated at 37° C.

RT-PCR

The following primer pairs were designed to specifically identify the presence of edg1, edg2, edg3, edg4, edg5, edg6, edg7 and edg8 gene expression in neurospheres, lateral venticle wall (LVW), and the rest of the brain (ROB) following LVW dissection. Primers are written 5'→3'. Estimated band sizes for each primer pair are given below:

|   |   | Band size (base pairs) |
|---|---|---|
| Edg1 | Fw: AAAACCAAGAAGTTCCACCGGCCC (SEQ ID NO:1) | 639 |
|   | Rev: GGCCTTGCAGCCCACATCTAACAGT (SEQ ID NO:2) |   |
| Edg2 | Fw: CAGCTGCCTCTACTTCCAGCCCTGTAATTT (SEQ ID NO:3) | 509 |
|   | Rev: GATGACTACAATCACCACCACCACGCGA (SEQ ID NO:4) |   |
| Edg3 | Fw: TTTCATCGGCAACTTGGCTCTCTGC (SEQ ID NO:5) | 635 |
|   | Rev: GGACAGCCAGCATGATGAACCACTG (SEQ ID NO:6) |   |
| Edg4 | Fw: ATGGGCCAGTGCTACTACAACGAGACCA (SEQ ID NO:7) | 509 |
|   | Rev: CAGAGGCAGTGCCAGAAGTGTGCAGGTA (SEQ ID NO:8) |   |
| Edg5 | Fw: GGCCTTCGTGGCCAACACCTTACT (SEQ ID NO:9) | 629 |
|   | Rev: CCCGGCTACGCCACGTATAGATGAC (SEQ ID NO:10) |   |
| Edg6 | Fw: ATGAACATCAGTACCTGGTCCACGCTGG (SEQ ID NO:11) | 513 |
|   | Rev: GCACAGACCGATGCAGCCATACAGAC (SEQ ID NO:12) |   |

-continued

| | | Band size (base pairs) |
|---|---|---|
| Edg7 | Fw: TGAATGAGTGTCACTATGACAAGCGCATGG (SEQ ID NO: 13) | 515 |
| | Rev: GTTGCAGAGGCAATTCCATCCCAGC (SEQ ID NO:14) | |
| Edg8 | Fw: CGGCGCCGGTGAGTGAGGTTATTGT (SEQ ID NO:15) | 514 |
| | Rev: AGGCGTCCTAAGCAGTTCCAGCCCA (SEQ ID NO:16) | |
| Actin | Fw: ATGGATGACGATATCGCTGCGCTGG (SEQ ID NO:17) | 360 |
| | Rev: GGTCATCTTTTCACGGTTGGCCTTAGGGT (SEQ ID NO:18) | |

Neurospheres were prepared from the LVW as stated above. 3 days after the first split, the neurospheres were harvested and total RNA isolated using Qiagen's RNeasy Mini Kit according to the manufacturer's instructions. LVW and ROB total RNA was prepared in identical fashion to that of neurosphere total RNA. Prior to the RT-PCR, total RNA was DNase (Ambion) treated (1 unit/5 µg total RNA) at 37° C. for 15 min, followed by heat inactivation at 75° C. for 10 min. Invitrogen's One-Step RT-PCR Kit was used to detect the presence of mRNA corresponding to the eight EDG receptors. Briefly, 12.5 ng of total RNA was used in each reaction, with an annealing temperature of 58° C. To further ensure that genomic contamination of the total RNA did not give rise to false positive results, an identical reaction in which the RT-taq polymerase mix was replaced by Taq polymerase alone was run in parallel with the experimental RT-PCR. The reactions were electrophoresed on a 1.0% agarose gel containing ethidium bromide and the bands visualised under UV light. Bands corresponding to the estimated length of PCR products of the desired genes were cloned into the cloning vector pGEM-Teasy and sequenced to verify their identity.

Results

Figure 1B:
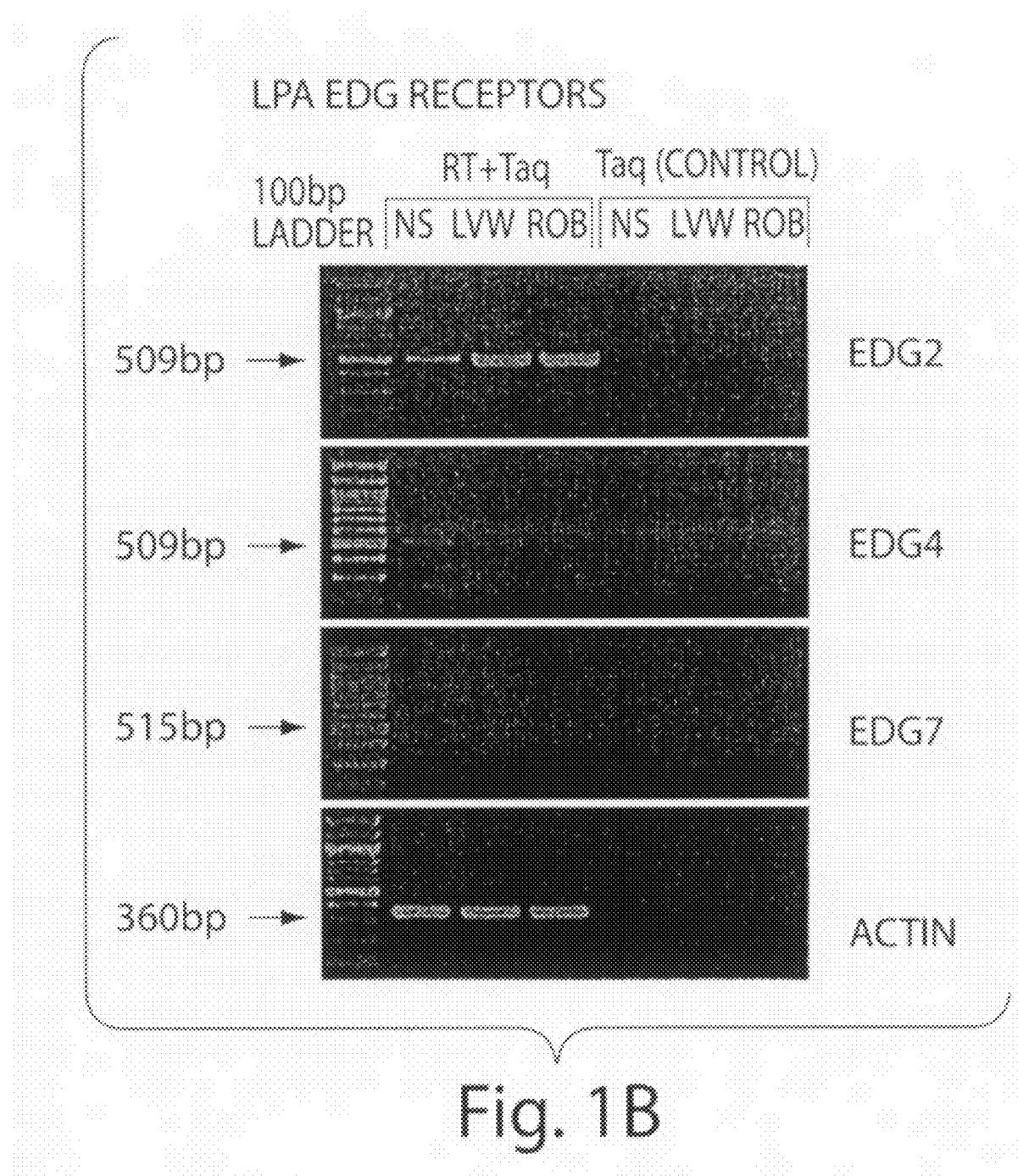

To determine whether the EDG receptors are expressed in the LVW and neural stem cells of adult mice, LVW tissue was harvested from adult mice and either used to prepare total RNA or to cultivate neurospheres from which RNA was then extracted. RT-PCR, using the prepared RNA, was performed, indicating gene expression of edg1, edg3 and edg8 in LVW, and edg1, edg3 and edg5 in neurospheres, of the S1P subclass EDG receptors (FIG. 1A). Of the LPA subclass of EDG receptors, edg2, edg4 and edg7 were present in LVW and edg2 and edg4 in neurospheres (FIG. 1B).

Example 2

EDG Receptors 1 & 8 are Expressed in Neurogenic Regions in the Adult Mouse Brain Methods
Radioactive In Situ Hybridization Whole brain from 6 weeks old mice were dissected out and frozen at −80° C. Sections (14 µm) of whole mouse brain were cut on a cryostat at −17° C., thawed onto microscope slides (Superfrost Plus, BDH, UK) and fixed in 4% formaldehyde for 5 min, deproteinated for 15 min in 0.2 M HCl, treated in 0.25% acetic anhydride in 0.1 M triethanolamine buffer, pH 8.0 for 20 min and dehydrated in an ascending series of ethanol concentrations including a 5 min chloroform step prior to hybridization. To detect Edg1, 8 mRNA, antisense cRNA probes were transcribed from plasmids (pGEM-Teasy) containing Edg1 and Edg8 cDNA (172 bp corresponding to bases 936 to 1107 of the coding sequence of mouse Edg1 gene, 294 bp corresponding to bases 55 to 384 of the coding sequence of mouse Edg8 gene) and concurrently [$\alpha$-$^{35}$S]UTP-labeled. The sections were incubated with the probe at 55° C. for 16 h in a hybridization buffer containing 52% formamide, 10% Dextran Sulfate, 208 mM NaCl, 2% 50×Denhardt's solution (1% Ficoll, 1% polyvinylpyrrolidene, 1% BSA) 10 mM Tris pH 8.0, 1 mM EDTA, 500 ng/ml yeast tRNA, 10 mM dithiothreitol (DTT) and $20 \times 10^6$ cpm probe per ml buffer. After hybridization, the sections were treated with RNase A, 10 µg/ml in 0.5 M NaCl, at 37° C. for 30 min and washed in 4×saline sodium citrate (SSC; 1×SSC is 0.15 M sodium chloride, 0.015 M trisodium citrate pH 7.0) for 20 min, 2×SSC for 10 min., 1×SSC for 10 min. and 0.5×SSC for 10 min. at room temperature. A high stringency wash was carried out at 70° C. for 30 min in 0.1×SSC. All wash steps included the addition of 1 mM DTT. The sections were dehydrated in an ascending series of ethanol concentrations, dried over night and mounted in cassettes with autoradiographic films (Beta-max, Amersham) placed on top for 3 weeks. The films were developed in Kodak D-19 developer, fixed in Kodak RA-3000 diluted 1:3, rinsed and dried. The sections were then dipped in Kodak NTB-2 nuclear track emulsion diluted 1:1, exposed for six weeks, developed in Kodak D-19 for 3 min., fixed in Kodak RA-3000 fixer and counterstained with cresyl violet. The specificity of the hybridization was tested using a sense probe transcribed from the same plasmid. No hybridization signal was obtained under this condition. The emulsion dipped sections were analysed manually using a Nikon E600 microscope.

Results

Figure 2A:
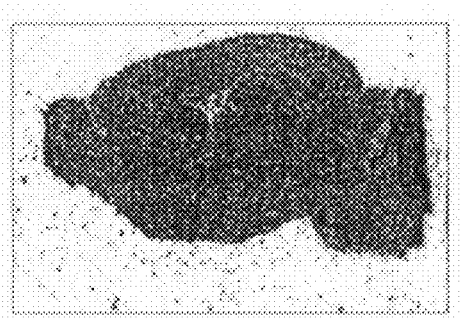
FIG. 2 shows brightfield and darkfield micrographs of edg1 mRNA positive cells in sagittal sections of adult mouse brain.
Figure 2B:
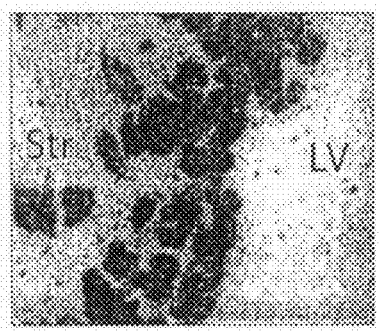
Figure 2C:
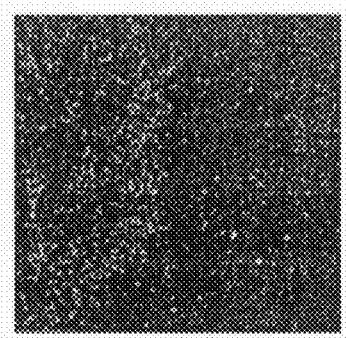

FIG. 2 represents brightfield and darkfield micrographs of edg1 mRNA positive cells in sagittal sections of adult mouse brain using an edg1 specific probe. FIG. 2A is a low magnification photograph showing edg1 expression in the lateral ventricle wall and the rostral migratory stream. FIGS. 2B & C shows higher magnification of the lateral ventricle wall. Note the positively labelled cells in the subventricular zone of the lateral ventricle wall. Abbreviations: LV, lateral ventricle; LVW, lateral ventricle wall; RMS, rostral migratory stream; Str, striatum; SVZ, subventricular zone.

Figure 3A:
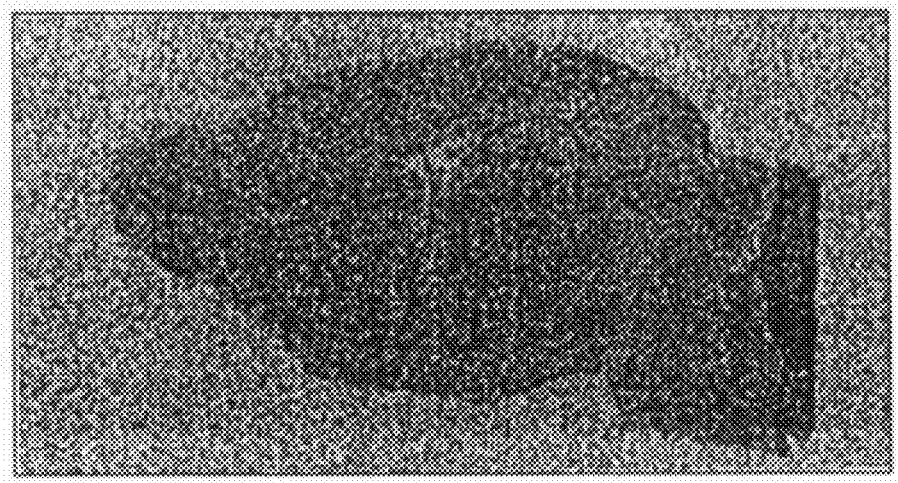
FIG. 3 shows low magnification microphotographs of edg8 mRNA expression in sections of the adult mouse brain.
Figure 3B:
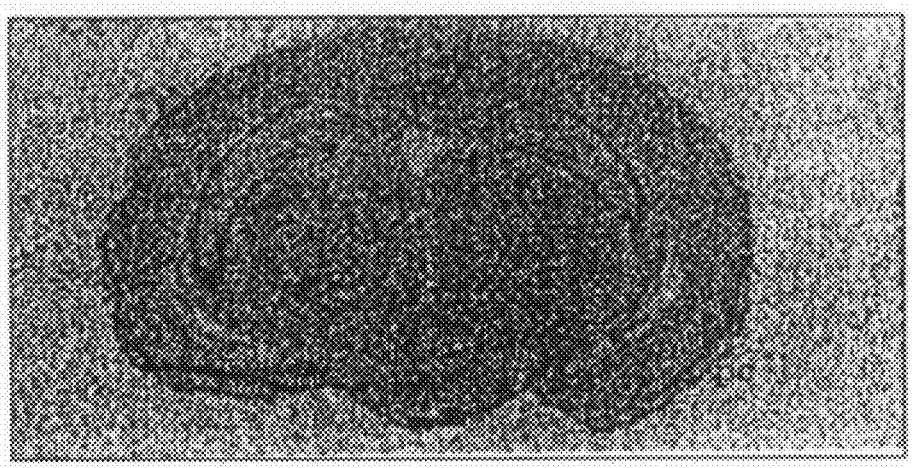

FIG. 3 shows low magnification microphotographs of edg8 mRNA expression in sections of adult mouse brain using an edg1 specific probe. FIGS. 3A & B show edg8 expression in the dentate gyrus and CA1-3 regions of the hippocampus. FIG. 3B also shows expression in the of edg8 in the piriform cortex. higher magnification of the lateral ventricle wall. Abbreviations: hp, hippocampus; pc, piriform cortex.

Example 3

S1P and LPA Stimulate Adult Mouse NSC Proliferation In Vitro

Methods
Mouse Neurosphere Cultures

The anterior lateral wall of the lateral ventricle of 5-6 week old mice was enzymatically dissociated in 0.8 mg/ml hyaluronidase and 0.5 mg/ml trypsin in DMEM containing 4.5 mg/ml glucose and 80 units/ml DNase at 37° C. for 20 min. The cells were gently triturated and mixed with three volumes of Neurosphere medium (DMEM/F12, B27 supplement, 12.5 mM HEPES pH7.4) containing 20 ng/ml EGF (unless otherwise stated), 100 units/ml penicillin and 100 µg/ml streptomycin. After passing through a 70 µm strainer, the cells were pelleted at 160×g for 5 min. The supernatant was subsequently removed and the cells resuspended in Neurosphere medium supplemented as above, plated out in culture dishes and incubated at 37° C. Neurospheres were ready to be split approximately 7 days after plating.

To split neurosphere cultures, neurospheres were collected by centrifugation at 160×g for 5 min. The neurospheres were resuspended in 0.5 ml Trypsin/EDTA in HBSS (1×), incubated at 37° C. for 2 min and triturated gently to aid dissociation. Following a further 3 min incubation at 37° C. and trituration, 3 volumes of ice cold NSPH-media-EGF were added to stop further trypsin activity. The cells were pelleted at 220×g for 4 min, resuspended in fresh Neurosphere medium supplemented with 20 ng/ml EGF and 1 nM bFGF plated out and incubated at 37° C.

Chemicals for dissociation of tissue; Trypsin, Hyaluronidase and DNase were from SIGMA. Medium (DMEM 4,5 mg/ml glucose, and DMEM/F12), B27 supplement and Trypsin/EDTA were from GIBCO. All plastic ware were purchased from CorningCostar. EGF for cell cultures was from BD Biosciences.

Where stated, a minimal Neurosphere medium was used containing BIT supplement in place of B27 supplement.

Intracellular ATP Assay

Intracellular ATP levels have previously been shown to correlate to cell number (Crouch, Kozlowski et al. 1993). Mouse neurospheres, cultured as described above, from passage 2, were seeded in DMEM/F12 supplemented with B27 into a 96-well plate as single cells (10000 cells/well) to the substances to be measured were added at the concentrations indicated. After 3 days incubation, intracellular ATP was measured using the ViaLight kit (BioWhittaker) according to the manufacturer's instructions. S1P and LPA were purchased from Avanti Polar Lipids, Inc.

In assays including pertussis toxin, the toxin was added at 100 ng/ml 24 hours prior to the second passaging. New toxin was added at the same dose in combination with S1P or LPA to the cells and assayed as described above.

In the experiment analysing the combinatory effect of S1P and EGF, S1P at 100 nM was co-incubated with 0.1 nM EGF for 3 days.

Thymidine Incorporation

To determine thymidine incorporation into DNA, neurospheres were split and seeded in Neurosphere medium as single cells in 96-well plates, 10 000 cells/well. Substances to be measured were added in quadruplicates and cells were incubated at 37° C. for 3 days. 3H-thymidine, 10 uCi/ml, was present the last 24 hours. Cells were harvested on to a filter paper and radioactivity was measured. 3H-thymidine (6,7 Ci/mmol) was from PerkinElmer.

Results

S1P Stimulates Adult Mouse NSC Proliferation In Vitro

Figure 4A:
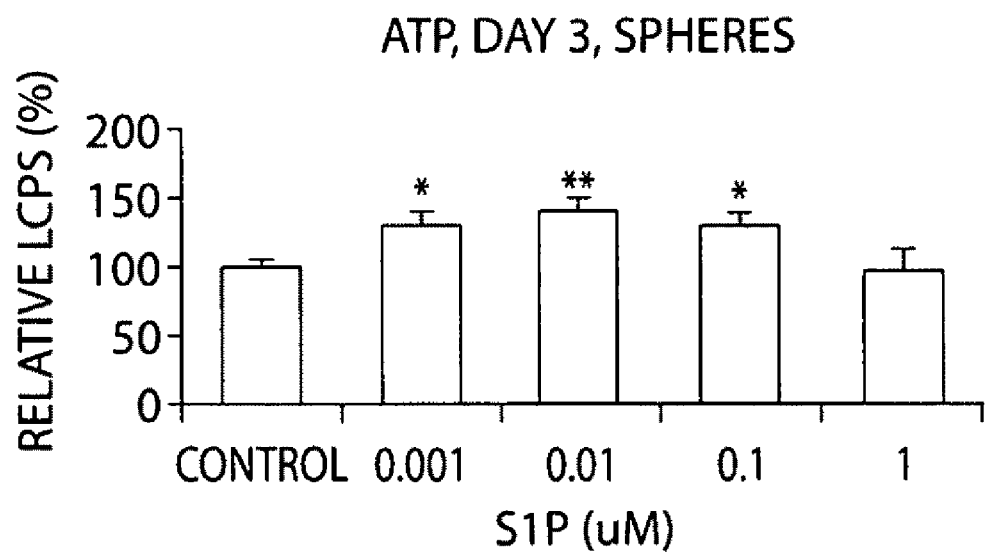
FIG. 4 shows that S1P stimulates in vitro proliferation of adult mouse NSC.
Figure 4B:
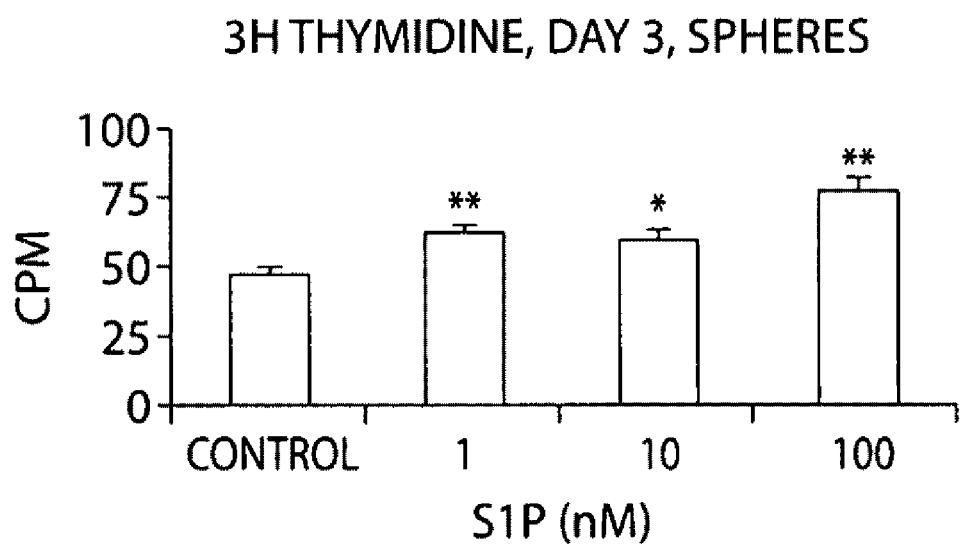

To determine the effect of S1P on neural stem cells in culture, mouse adult neural stem cells derived from the lateral ventricle wall of the brain, expanded in EGF as neurospheres followed by enzymatic dissociation using trypsin, were cultured in Neurosphere medium supplemented with varying concentrations of S1P, under non-adherent conditions, for 3 days. To ascertain whether there was an increase in cell number of S1P treated cells relative to control cells, an assay measuring intracellular ATP levels, shown previously to correlate with cell number (Crouch, Kozlowski et al. 1993), was employed. FIG. 4A shows a statistically significant increase in intracellular ATP levels, and hence cell number, in response to S1P at nanomolar (1-100 nM) concentrations. To ascertain whether the effect of S1P is through proliferation, incorporation of tritiated thymidine was used to assess DNA synthesis in NSC. Greater incorporation of tritiated thymidine was observed with S1P between 1-100 nM concentrations relative to control, indicating that S1P is eliciting a proliferating response in NSC under non-adherent conditions (FIG. 4B). The increase in cell number, however, does not rule out an additional survival effect of S1P on NSC. Data shown in FIG. 4 are from experiments performed in sextuplicate (A) and octuplicate (B). Bars represent SEM. Levels of significance of increases above control were determined by a paired Student t test; * $P<0.05$, ** $P<0.005$.

LPA Stimulates Adult Mouse NSC Proliferation In Vitro

Figure 5A:
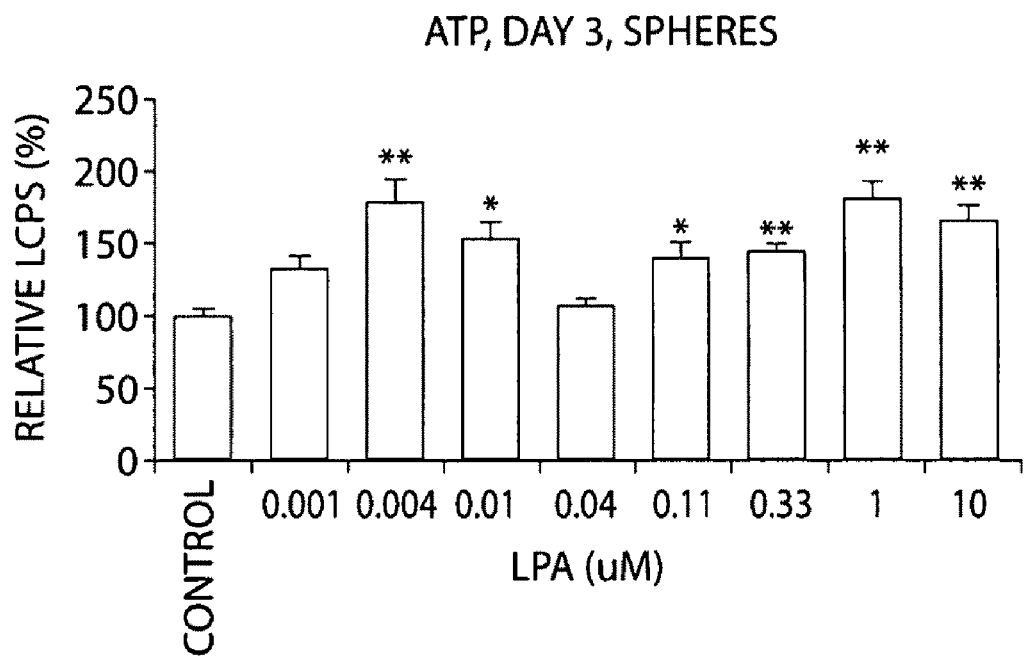
FIG. 5 shows that LPA stimulates in vitro proliferation of adult mouse NSC.

To determine the effect of LPA on neural stem cells in culture, mouse adult neural stem cells derived from the lateral ventricle wall of the brain, expanded in EGF as neurospheres followed by enzymatic dissociation using trypsin, were cultured in Neurosphere medium supplemented with varying concentrations of LPA, under non-adherent conditions, for 3 days. To ascertain whether there was an increase in cell number of LPA treated cells relative to control cells, an assay measuring intracellular ATP levels, shown previously to correlate with cell number (Crouch, Kozlowski et al. 1993), was employed. FIG. 5A shows statistically significant increases in intracellular ATP levels, and hence cell number, in response to LPA, but that this response is entirely dependent on the concentration of LPA. The concentration dependent effect of LPA on NSC can be divided into two distinct phases, one at low concentration (1-10 nM), and the other at higher concentrations (0,11-10 µM). This biphasic response could reflect the nature of the ligand, signalling through the receptors at low concentration and functioning as an intracellular signalling molecule, after diffusing through the cell plasma membrane at higher concentration.

Figure 5B:
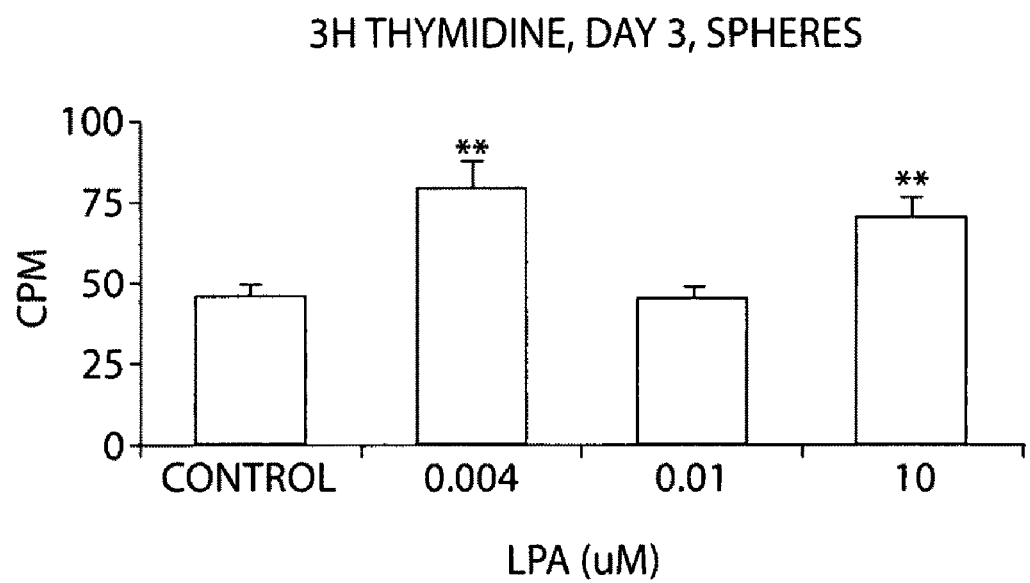

To ascertain whether the effect of LPA is through proliferation, incorporation of tritiated thymidine was used to assess DNA synthesis in NSC. Greater incorporation of tritiated thymidine was observed with LPA at 4 nM and 10 µM concentrations relative to control, however, no significant incorporation occurred at 10 nM (FIG. 5B).

Data shown in FIG. 5 are from experiments performed in sextuplicate (A) and octuplicate (B). Bars represent ±SEM. Levels of significance of increases above control were determined by a paired Student t test; * $P<0.05$, ** $P<0.005$.

The Proliferating Effect of S1P on NSC is Mediated Through G Protein-Coupled Receptors Five high affinity receptors for S1P have been described, EDG1, EDG3, EDG5, EDG6 and EDG8, within the EDG family, which in turn is categorised within the G protein-coupled receptor (GPCR) superfamily (Pyne and Pyne 2000). Pertussis toxin (PTX) specifically inactivates $G_i$ and $G_o$ proteins by ADP-ribosylation of $\alpha_i$ subunit, uncoupling the GPCRs from their effector mechanisms. Mitogenic effects of S1P interaction with its receptors have previously been shown to be inhibited by PTX (Goetzl, Dolezalova et al. 1999; An, Zheng et al. 2000; Pyne and Pyne 2000; Yamazaki, Kon et al. 2000; Kluk and Hla 2001).

Figure 6:
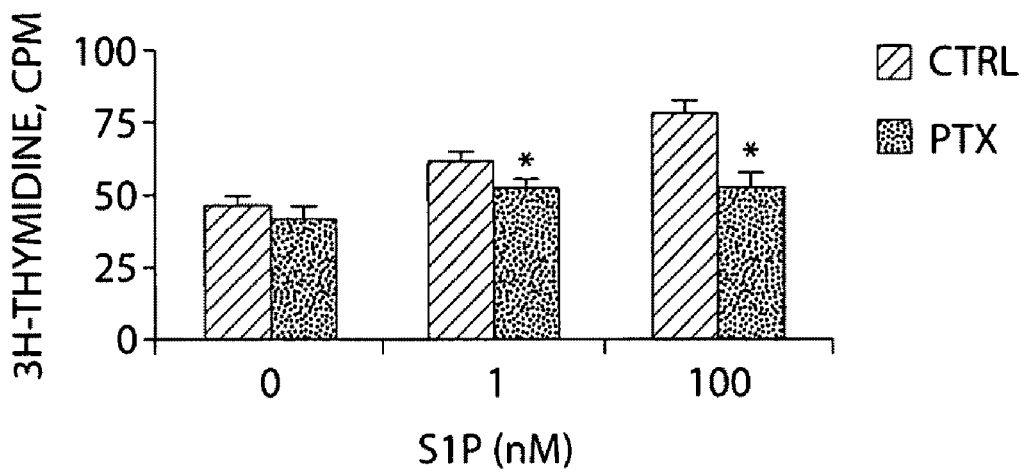
FIG. 6 shows that the effect of S1P on adult mouse NSC proliferation is inhibited by pertussis toxin (PTX).

To investigate whether PTX abolishes the proliferating effect of S1P on NSC, incorporation of 3-H thymidine was assayed. PTX completely inhibited the proliferating effect of S1P at both low and high doses (FIG. 6). These data indicate that S1P's proliferating effect is mediated through GPCRs coupled to $G_i$ and $G_o$ proteins, a criteria fulfilled by S1P's receptors.

Data shown are from experiments performed in octuplicate. Bars represent ±SEM. Levels of significance of increases above control were determined by a paired Student t test; * P<0.06.

The Proliferating Effect of LPA on NSC is Mediated Through G Protein-Coupled Receptors at Low Concentration Three high affinity receptors for LPA have been described, EDG2, EDG4 and EDG7, within the EDG family, which in turn is categorised within the G protein-coupled receptor (GPCR) superfamily (Fukushima and Chun 2001). Pertussis toxin (PTX) specifically inactivates $G_i$ and $G_o$ proteins by ADP-ribosylation of αi subunit, uncoupling the GPCRs from their effector mechanisms. Mitogenic effects of LPA interaction with its receptors have previously been shown to be inhibited by PTX (Goetzl, Dolezalova et al. 1999; Grey, Banovic et al. 2001).

Figure 7:
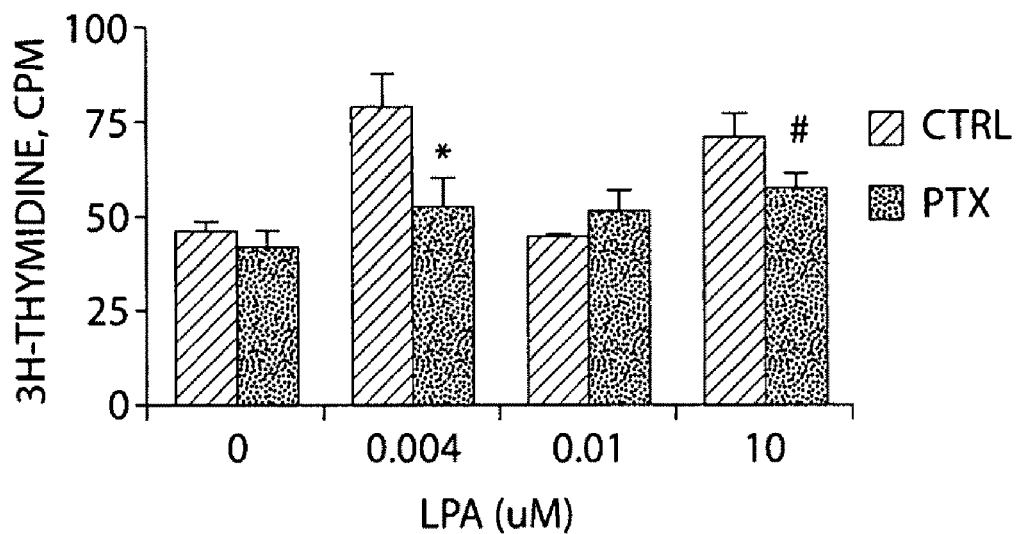
FIG. 7 shows that the effect of LPA on adult mouse NSC proliferation is inhibited by pertussis toxin (PTX).

To investigate whether PTX abolishes the proliferating effect of LPA on NSC, incorporation of 3-H thymidine was assayed. PTX abolished the proliferating effect of LPA at low concentration (4 nM), however, at high concentration (10 μM) PTX had no significant inhibitory effect (FIG. 7). These data indicate that LPA's proliferating effect at low concentration is mediated through GPCRs coupled to $G_i$ and $G_o$ proteins, a criteria fulfilled by LPA's receptors. At high LPA concentration, proliferation of NSC appears to be, at least partly, a non-GPCR mediated event. This conclusion is not at odds with the hypothesis that at high concentration the dominant effect of LPA is as an intracellular signalling molecule rather than a ligand of the EDG receptors. Alternatively, the effect of LPA could be as a consequence of altered membrane fluidity, or functioning as a modulator of ligand/hormone affinity for their receptors (eg nuclear receptor).

Data shown are from experiments performed in octuplicate. Bars represent ±SEM. Levels of significance relative to control (*), or level of significance comparing PTX with and without LPA (#) were determined by a paired Student t test; * P<0.05; # P<0.05.

S1P and EGF Synergistically Proliferate Adult Mouse NSC In Vitro

Figure 8:
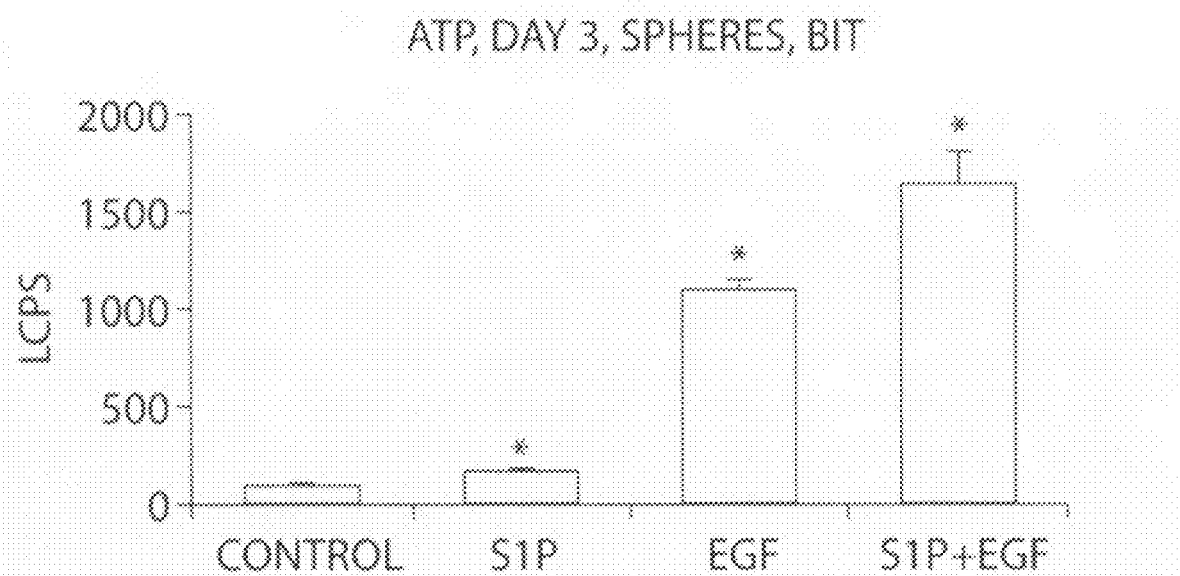
FIG. 8 shows that S1P and EGF synergistically proliferate adult mouse NSC in vitro.

NSC were treated with S1P, EGF or a combination of the two. While either of the two factors alone increased intracellular ATP levels, and hence NSC number, when combined, there was a further elevation the values of which are indicative of a synergistic effect between the two factors (FIG. 8). Data shown are from experiments performed in quadruplet. Bars represent ±SEM. Levels of significance of increases above control were determined by a paired Student t test; * P<0.05.

Figure 9:
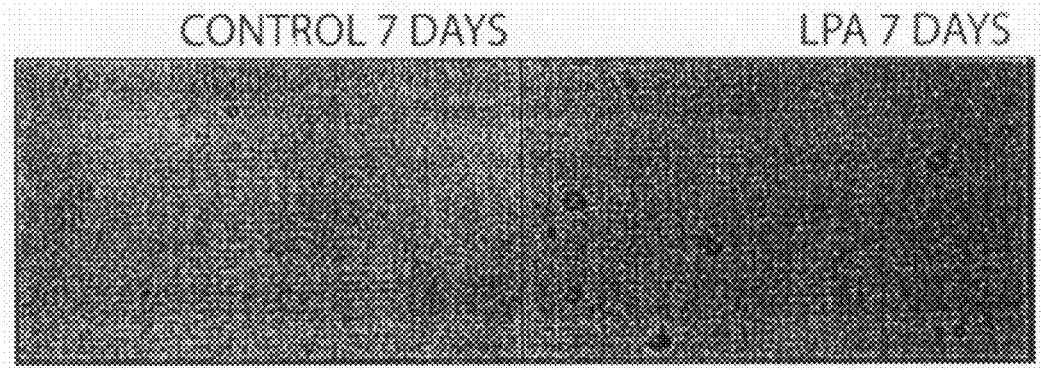
FIG. 9 shows LPA stimulates primary adult mouse NSC proliferation and neurosphere formation in vitro

LPA Stimulates Primary Adult Mouse NSC to Proliferate, Forming Neurospheres, in the Absence of Growth Factors Anterior lateral wall of the lateral ventricle was dissociated as described in the Methods above (Method A), and the cells resuspended in Neurosphere medium without EGF. The cell suspension was divided into a 24-well plate with triplicates of control (no addition), LPA treated and EGF (1 nM) treated cells. The final concentration of LPA was 10 μM. After 7 days the spheres were counted, inspected for growth and morphology and photographed using a Nikon Eclipse TE300 microscope and Nikon Spot Insight camera. FIG. 9 shows NSC treated with LPA growing in a neurosphere formation, the sizes and number of which were observably greater than that of the control.

Example 4

S1P Increases the Number of New-Born Cells in the Caudate Putamen of Adult Rats

Methods

Animals

Arrival of animals: 06.1102 (30 animals), 13.11.02 (30 animals) and 20.11.02 (10 animals): Male Wistar rats, ca.270g, Harlan-Winkelmann Germany;

Animal housing: 12 hours light/dark regime; feeding: standard pellets; feeding and drinking ad libitum; 5 animals in standard cage (Macrolon typeM4)

Preparation of Pump

Brain infusion kit II; Alzet osmotic mini-pump model 2002 (volume of pump: 200 μl, plus ca. 30-50 μl volume in tubing/flow-moderator; pumping rate: 0.5 μl/h (=12 μl/d) for 14 days; vehicle solution aCSF (artificial cerebrospinal fluid: 148 mM NaCl, 3 mM KCl, 1.4 mM $CaCl_2$, 0.8 mM $MgCl_2$, 1.5 mM $Na_2HPO_4$, 0.2 mM $NaH_2PO_4$, pH 7.4, steril filtration; stored at −20° C.

Handling of Substances:

| group no | cmp provided as | compound | stock in | stock conc, mM | in vitro EC50, nM |
|---|---|---|---|---|---|
| 1 | solid | S1P | DMSO | 10 | 30 |
| 2 | n.a. | control 2/0, 1% DMSO | n.a. | | |

| final pump conc, microM | Mol weight | stock solution prep | pump solution prep | compound |
|---|---|---|---|---|
| 10 | 379 | 1 mg/0.264 ml | | S1P |

S1P
provided as 1 mg solid, dissolved in DMSO, aliquoted and kept in freezer,
thawed and added aCSF to make pump solution, 0.1% DMSO maximum.

Before filling pump the following was added: 50 μg/ml Gentamycin (Sigma) and BrdU (1 mg/BrdU/ml) at 37° C. and ultra-sonication, pump filled with 200 μl of aforementioned solution, connected via tubing to flow moderator (also filled with aforementioned solution); put in NaCl (0.9%) solution in water bath (37° C.) for 2-5 hrs before implantation (note time point).

For control animals pumps were filled with vehicle only (vehicle I: aCSF/Gentamycin/BrdU; vehicle II: aCSF/Gentamycin/BrdU/DMSO0.1%).

Operation:

Starting in week 48/2002; narcosis (inhalation) initially: halothane (4%) in $O_2/N_2O$ (50:50); animals fixed in stoelting stereotaxic frame, halothane adapted to 2-3%; cut skin and remove from skull; left posterior quadrant of skull: drill hole for screw (not touching dura); drill hole for cannula: 0.08 cm posterior to bregma; 0.17 cm lateral from satura sagittalis; insertion of canula: 0.45 cm below skull; fixation with dental cement (Paladur). Length of tubing: ca 10 cm. Storage of pump subcutaneously in midscapular region.

Animals put in cage (one animal/cage: Macrolon typeM3) and after recovery from anaesthesia back to animal housing.

Removal of Pumps:

14 days after insertion of pump: anaesthesia of animals with halothane (initially: 4%; operation performed at 2.0-2.5%) in $N_2O/O_2$ (50:50). Opening of suture. Cut tubing, removal of pump. Note time point of removal and suck rest of solution out of pump with syringe.

Decapitation:

Narcosis of animals with chloralhydrate (4 g/100 ml; 6 ml/animal); transcardial perfusion with NaCl for ca 3-5 minutes (ca 60 ml); perfusion with paraformaldehyd (4%) solution (3-5 min, ca 60 ml), decapitation; removal of brain stored in paraformaldehyd (4%) solution over night; transfer in 30% sucrose solution (in refrigerator) until brain sinks to bottom (ca. 3 days); freezing via −80° C. Methylbutan and storage in −80° C. freezer. Mark contralateral side with a notch Treatment:
(randomized, placebo-controlled)
group 1: BrdU/aCSF/Gentamycin/DMSO0.1%/S1P; 10 µM (0.12 nmol/d; 8 animals)
group 2: control—BrdU/aCSF/Gentamycin/DMSO 0.1% (12 animals)
decapitation 14 days after insertion of pump Slicing:

Cutting of rest of brain coronally 40 µm, (free floating) until level where ventricle is fully developed (bregma+0.7-0.5 mm (first signs of ventricle approximately +1.6-1.2 mm) slices between bregma+2.7 mm and ca. +0.7 mm will be lost). 10 slices will be taken in 4 tubes with CPS (250 ml Ethylenglycol, 250 ml Glycerol, PBS ad 1000 ml); (cannula track can not be checked. Store at 4° C.

Immunohistochemistry:
DAB (diaminobenzidine) staining:
(with two slices: one from beginning, one from end of slice-collection)
slices in PBS 0.1M
inactivate endogenous peroxidase for 30 min(solution freshly prepared):
50% Methanol
50% PBS 0.1M
3% $H_2O_2$
washing in PBS: 3×5 min
washing in PBS: 3×5 min
incubation in 2N HCl for 30 min (37° C.)
washing in PBS: 4×5 min
Incubation in blocking-serum for 60 min at RT:
300 µl donkey normal serum (DNS)
2700 µl PBS 0.1 M/TritonX100 0.5%
primary antibody at 4° C. over night: incubation with rat anti BrdU (1:500):
988 µl PBS 0.1M
10 µl DNS
2 µl rat anti BrdU
washing in PBS: 3×10 min
secondary antibody for 1 h at RT (prepared 30 min before using)
988 µl PBS 0.1M
2 µl donkey anti rat biotinylated
washing in PBS: 3×5 min
incubation with Vector Elite Kit 1 h at RT (prepared 30 min before using)
4000 µl PBS 0.1M
10 µl sol. A
10 µl sol. B
washing in PBS: 3×5 min
Incubation for ca 5-10 min in:
5 mg DAB
10 ml PBS 0.1M
2 µl $H_2O_2$ (30%)
washing in PBS: 3×5 min
microscope slide, drying, EtOH, Xylol, glascoverslips Quantification:

Quantification in ipsilateral hemisphere: two slices (see point "Immunohistochemistry") counting 2×one box (0.25 mm$^2$) in caudate putamen on each section.

Results

S1P Increases the Number of New Born Cells in the Caudate Putamen

Figure 10:
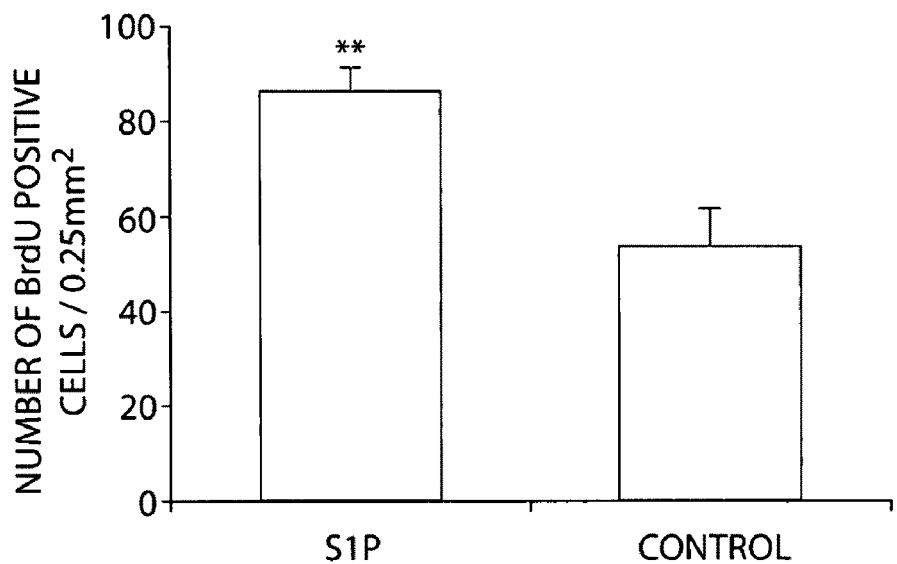
FIG. 10 shows that S1P increases the number of newborn cells in the caudate putamen of adult rats
Figure 11:
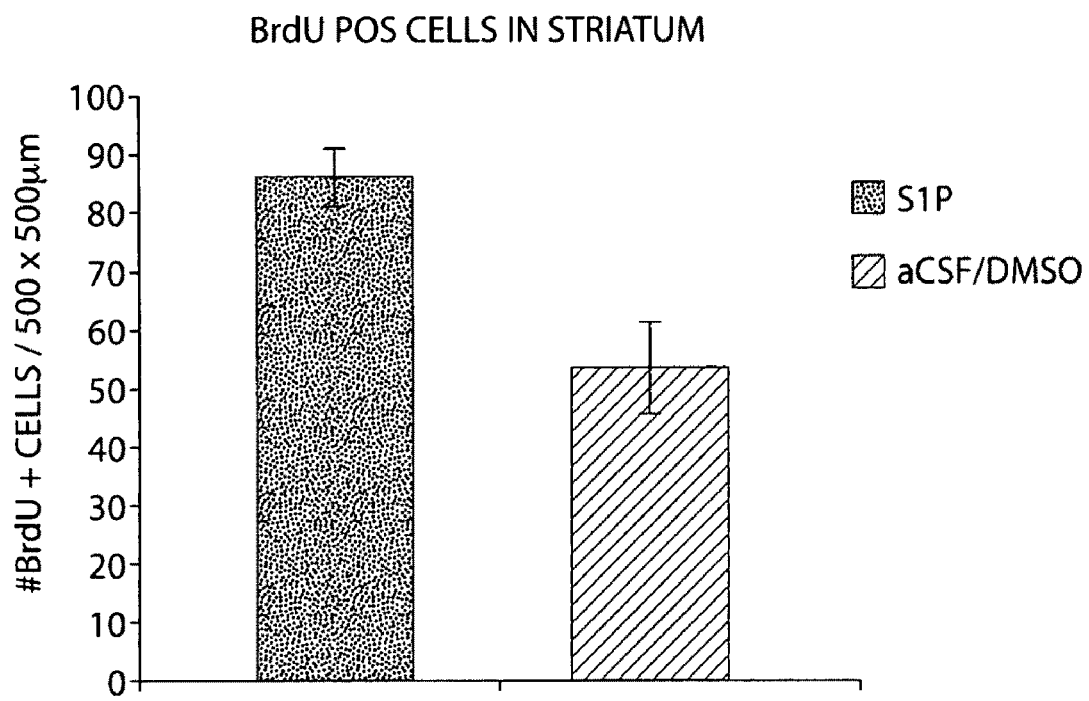
FIG. 11 shows that S1P increases the number of BrdU positive cells in the caudate putamen.

S1P (10 µM pump concentration) or vehicle, and BrdU (1 mg/ml pump concentration) was infused into the lateral ventricle of adult male Wistar rats at a rate of 0.5 µ/hr for 14 days. BrdU incorporation into the nuclei of dividing cells is a standard method of labeling proliferating populations of cells, and has become a well used marker for dividing stem cells and their progeny (Zhang, Zhang et al. 2001). BrdU incorporated into the nuclei of proliferating cells was detected by DAB-immunohistochemistry. Coronal sections through the caudate putamen showed BrdU labeling of a substantially greater number of cells in S1P treated rats relative to rats treated with vehicle. For quantification (FIG. 10), sections were taken in duplicate for each animal and counted manually (see above Methods). Results are expressed as the mean ±SEM number of BrdU positive cells/0.25 mm$^2$ (S1P n=8) (Vehicle n=12) (**$p<0.005$ relative to Vehicle). The quantitative data show a significant increase in the number new born cells in the caudate putamen upon S1P treatment relative to vehicle.

Example 5

Biopolymer Sequences

The DNA and protein sequences referenced in this patent are as listed below.

A. EDG1 Locus Link ID: 1901 (human); 13609 (mouse)

| GenBank Accession Number | Description |
| --- | --- |
| NM_001400 | *Homo sapiens* endothelial differentiation, sphingolipid G-protein-coupled receptor, 1, mRNA (EDG1) |
| NM_007901 | *Mus musculus* endothelial differentiation, sphingolipid G-protein-coupled receptor, 1, mRNA (Edg1) |
| NP_001391 | *Homo sapiens* endothelial differentiation, sphingolipid G-protein-coupled receptor, 1, (EDG1) |
| NP_031927 | *Mus musculus* endothelial differentiation, sphingolipid G-protein-coupled receptor, 1, (Edg1) |

B. EDG2 Locus Link ID: 1902 (human); 14745 (mouse)

| GenBank Accession Number | Description |
| --- | --- |
| NM_001401 | *Homo sapiens* endothelial differentiation, sphingolipid G-protein-coupled receptor, 2, mRNA (EDG2) |
| NM_057159 | |

-continued

| GenBank Accession Number | Description |
| --- | --- |
| NM_010336 | *Mus musculus* endothelial differentiation, sphingolipid G-protein-coupled receptor, 2, mRNA (Edg2) |
| NP_001392 | *Homo sapiens* endothelial differentiation, sphingolipid G-protein-coupled receptor, 2, (EDG2) |
| NP_476500 | |
| NP_14745 | *Mus musculus* endothelial differentiation, sphingolipid G-protein-coupled receptor, 2, (Edg2) |

C. EDG3 Locus Link ID: 1903 (human); 13610 (mouse)

| GenBank Accession Number | Description |
| --- | --- |
| NM_005226 | *Homo sapiens* endothelial differentiation, sphingolipid G-protein-coupled receptor, 3, mRNA (EDG3) |
| NM_010101 | *Mus musculus* endothelial differentiation, sphingolipid G-protein-coupled receptor, 3, mRNA (Edg3) |
| NP_005217 | *Homo sapiens* endothelial differentiation, sphingolipid G-protein-coupled receptor, 3, (EDG3) |
| NP_034231 | *Mus musculus* endothelial differentiation, sphingolipid G-protein-coupled receptor, 3, (Edg3) |

D. EDG4 Locus Link ID: 9170 (human); 53978 (mouse)

| GenBank Accession Number | Description |
| --- | --- |
| NM_004720 | *Homo sapiens* endothelial differentiation, sphingolipid G-protein-coupled receptor, 4, mRNA (EDG4) |
| NM_020028 | *Mus musculus* endothelial differentiation, sphingolipid G-protein-coupled receptor, 4, mRNA (Edg4) |
| NP_004711 | *Homo sapiens* endothelial differentiation, sphingolipid G-protein-coupled receptor, 4, (EDG4) |
| NP_064412 | *Mus musculus* endothelial differentiation, sphingolipid G-protein-coupled receptor, 4, (Edg4) |

E. EDG5 Locus Link ID: 9294 (human); 14739 (mouse)

| GenBank Accession Number | Description |
| --- | --- |
| NM_004230 | *Homo sapiens* endothelial differentiation, sphingolipid G-protein-coupled receptor, 5, mRNA (EDG5) |
| XM_134731 | *Mus musculus* endothelial differentiation, sphingolipid G-protein-coupled receptor, 5, mRNA (Edg5) |
| NP_004221 | *Homo sapiens* endothelial differentiation, sphingolipid G-protein-coupled receptor, 5, (EDG5) |
| XP_134731 | *Mus musculus* endothelial differentiation, sphingolipid G-protein-coupled receptor, 5, (Edg5) |

F. EDG6 Locus Link ID: 8698 (human); 13611 (mouse)

| GenBank Accession Number | Description |
| --- | --- |
| NM_003775 | *Homo sapiens* endothelial differentiation, sphingolipid G-protein-coupled receptor, 6, mRNA (EDG6) |
| NM_010102 | *Mus musculus* endothelial differentiation, sphingolipid G-protein-coupled receptor, 6, mRNA (Edg6) |
| NP_003766 | *Homo sapiens* endothelial differentiation, sphingolipid G-protein-coupled receptor, 6, (EDG6) |
| NP_034232 | *Mus musculus* endothelial differentiation, sphingolipid G-protein-coupled receptor, 6, (Edg6) |

G. EDG7 Locus Link ID: 23566 (human); 65086 (mouse)

| GenBank Accession Number | Description |
| --- | --- |
| NM_012152 | *Homo sapiens* endothelial differentiation, sphingolipid G-protein-coupled receptor, 7, mRNA (EDG7) |
| NM_022983 | *Mus musculus* endothelial differentiation, sphingolipid G-protein-coupled receptor, 7, mRNA (Edg7) |
| NP_036284 | *Homo sapiens* endothelial differentiation, sphingolipid G-protein-coupled receptor, 7, (EDG7) |
| NP_075359 | *Mus musculus* endothelial differentiation, sphingolipid G-protein-coupled receptor, 7, (Edg7) |

Splice Variant
Fitzgerald L R, Dytko G M, Sarau H M, Mannan I J, Ellis C, Lane P A, Tan K B, Murdock P R, Wilson S, Bergsma D J, Ames R S, Foley J J, Campbell D A, McMillan L, Evans N, Elshourbagy N A, Minehart H, Tsui P,
Identification of an EDG7 variant, HOFNH30, a G-protein-coupled receptor for lysophosphatidic acid.
Biochem Biophys Res Commun. 2000 Jul. 14; 273(3):805-10.

H. EDG8 Locus Link ID: 53637 (human); 94226 (mouse)

| GenBank Accession Number | Description |
| --- | --- |
| NM_030760 | *Homo sapiens* endothelial differentiation, sphingolipid G-protein-coupled receptor, 8, mRNA (EDG8) |
| NM_053190 | *Mus musculus* endothelial differentiation, sphingolipid G-protein-coupled receptor, 8, mRNA (Edg8) |
| NP_110387 | *Homo sapiens* endothelial differentiation, sphingolipid G-protein-coupled receptor, 8, (EDG8) |
| NP_444420 | *Mus musculus* endothelial differentiation, sphingolipid G-protein-coupled receptor, 8, (Edg8) |

REFERENCES

Altman, J. and G. Das (1965). "Autoradiographic and histological evidence of postnatal hippocampal neurogenesis in rats." *J Comp Neurol* 124: 319-335.

Altman, J. and G. Das (1967). "Postnatal neurogenesis in the guinea-pig." *Nature* 214: 1098-1101.

An, S., T. Bleu, et al. (1998). "Characterization of a novel subtype of human G protein-coupled receptor for lysophosphatidic acid." *J Biol Chem* 273(14): 7906-10.

An, S., T. Bleu, et al. (1997). "Identification of cDNAs encoding two G protein-coupled receptors for lysosphingolipids." *FEBS Lett* 417(3): 279-82.

An, S., Y. Zheng, et al. (2000). "Sphingosine 1-phosphate-induced cell proliferation, survival, and related signaling events mediated by G protein-coupled receptors Edg3 and Edg5." *J Biol Chem* 275(1): 288-96.

Aoki, J., K. Bandoh, et al. (2000). "A novel human G-protein-coupled receptor, EDG7, for lysophosphatidic acid with unsaturated fatty-acid moiety." *Ann N Y Acad Sci* 905: 263-6.

Bayer, S. A. (1986). "Neurogenesis in the rat primary olfactory cortex." *Int J Dev Neurosci* 4(3): 251-71.

Bernier, P. J., A. Bedard, et al. (2002). "Newly generated neurons in the amygdala and adjoining cortex of adult primates." *Proc Natl Acad Sci USA* 99(17): 11464-9.

Biebl, M., C. M. Cooper, et al. (2000). "Analysis of neurogenesis and programmed cell death reveals a self-renewing capacity in the adult rat brain." *Neurosci Lett* 291(1): 17-20.

Bjorklund, A. and O. Lindvall (2000). "Cell replacement therapies for central nervous system disorders." *Nat Neurosci* 3(6): 537-44.

Contos, J. J., N. Fukushima, et al. (2000). "Requirement for the lpA1 lysophosphatidic acid receptor gene in normal suckling behavior." *Proc Natl Acad Sci USA* 97(24): 13384-9.

Craig, C. G., V. Tropepe, et al. (1996). "In vivo growth factor expansion of endogenous subependymal neural precursor cell populations in the adult mouse brain." *J Neurosci* 16(8): 2649-58.

Crouch, S. P., R. Kozlowski, et al. (1993). "The use of ATP bioluminescence as a measure of cell proliferation and cytotoxicity." *J Immunol Methods* 160(1): 81-8.

Doetsch, F., I. Caille, et al. (1999). "Subventricular zone astrocytes are neural stem cells in the adult mammalian brain." *Cell* 97(6): 703-16.

Fukushima, N. and J. Chun (2001). "The LPA receptors." *Prostaglandins* 64(1-4): 21-32.

Gage, F. H., G. Kempermann, et al. (1998). "Multipotent progenitor cells in the adult dentate gyrus." *J Neurobiol* 36(2): 249-66.

Goetzl, E. J. and S. An (1998). "Diversity of cellular receptors and functions for the lysophospholipid growth factors lysophosphatidic acid and sphingosine 1-phosphate." *Faseb J* 12(15): 1589-98.

Goetzl, E. J., H. Dolezalova, et al. (1999). "Dual mechanisms for lysophospholipid induction of proliferation of human breast carcinoma cells." *Cancer Res* 59(18): 4732-7.

Graler, M. H., G. Bernhardt, et al. (1998). "EDG6, a novel G-protein-coupled receptor related to receptors for bioactive lysophospholipids, is specifically expressed in lymphoid tissue." *Genomics* 53(2): 164-9.

Grey, A., T. Banovic, et al. (2001). "Lysophosphatidic acid is an osteoblast mitogen whose proliferative actions involve G(i) proteins and protein kinase C, but not P42/44 mitogen-activated protein kinases." *Endocrinology* 142(3): 1098-106.

Hecht, J. H., J. A. Weiner, et al. (1996). "Ventricular zone gene-1 (vzg-1) encodes a lysophosphatidic acid receptor expressed in neurogenic regions of the developing cerebral cortex." *J Cell Biol* 135(4): 1071-83.

Herman, J. P. and N. D. Abrous (1994). "Dopaminergic neural grafts after fifteen years: results and perspectives." *Pros Neurobiol* 44(1): 1-35.

Hla, T. and T. Maciag (1990). "An abundant transcript induced in differentiating human endothelial cells encodes a polypeptide with structural similarities to G-protein-coupled receptors." *J Biol Chem* 265(16): 9308-13.

Im, D. S., C. E. Heise, et al. (2000). "Characterization of a novel sphingosine 1-phosphate receptor, Edg-8." *J Biol Chem* 275(19): 14281-6.

Jacobson, M. (1991). Histosenesis and morphogenesis of cortical structures. *Developmental Neurobiology*, Plenum Press, New York: 401-451.

Jalink, K., T. Eichholtz, et al. (1993). "Lysophosphatidic acid induces neuronal shape changes via a novel, receptor-mediated signaling pathway: similarity to thrombin action." *Cell Growth Differ* 4(4): 247-55.

Johansson, C. B., S. Momma, et al. (1999). "Identification of a neural stem cell in the adult mammalian central nervous system." *Cell* 96(1): 25-34.

Johansson, C. B., M. Svensson, et al. (1999). "Neural stem cells in the adult human brain."*Exp Cell Res* 253(2): 733-6.

Johe, K. K., T. G. Hazel, et al. (1996). "Single factors direct the differentiation of stem cells from the fetal and adult central nervous system." *Genes Dev* 10(24): 3129-40.

Kluk, M. J. and T. Hla (2001). "Role of the sphingosine 1-phosphate receptor EDG-1 in vascular smooth muscle cell proliferation and migration." *Circ Res* 89(6): 496-502.

Kuhn, H. G. and C. N. Svendsen (1999). "Origins, functions, and potential of adult neural stem cells." *Bioessays* 21(8): 625-30.

Kuhn, H. G., J. Winkler, et al. (1997). "Epidermal growth factor and fibroblast growth factor-2 have different effects on neural progenitors in the adult rat brain." *J Neurosci* 17(15): 5820-9.

Lee, M. J., J. R. Van Brocklyn, et al. (1998). "Sphingosine-1-phosphate as a ligand for the G protein-coupled receptor EDG-1." *Science* 279(5356): 1552-5.

Lois, C. and A. Alvarez-Buylla (1993). "Proliferating subventricular zone cells in the adult mammalian forebrain can differentiate into neurons and glia." *Proc Natl Acad Sci USA* 90(5): 2074-7.

Magavi, S. S., B. R. Leavitt, et al. (2000). "Induction of neurogenesis in the neocortex of adult mice [see comments]." *Nature* 405(6789): 951-5.

McGiffert, C., J. J. Contos, et al. (2002). "Embryonic brain expression analysis of lysophospholipid receptor genes suggests roles for s1p(1) in neurogenesis and s1p(1-3) in angiogenesis." *FEBS Lett* 531(1): 103-8.

McKay, R. (1997). "Stem cells in the central nervous system." *Science* 276(5309): 66-71.

Momma, S., C. B. Johansson, et al. (2000). "Get to know your stem cells." *Curr Opin Neurobiol* 10(1): 45-9.

Palmer, T. D., E. A. Markakis, et al. (1999). "Fibroblast growth factor-2 activates a latent neurogenic program in neural stem cells from diverse regions of the adult CNS." *J Neurosci* 19(19): 8487-97.

Pebay, A., M. Toutant, et al. (2001). "Sphingosine-1-phosphate induces proliferation of astrocytes: regulation by intracellular signalling cascades." *Eur J Neurosci* 13(12): 2067-76.

Pencea, V., K. D. Bingaman, et al. (2001). "Infusion of Brain-Derived Neurotrophic Factor into the Lateral Ventricle of the Adult Rat Leads to New Neurons in the Parenchyma of the Striatum, Septum, Thalamus, and Hypothalamus." *J Neurosci* 21(17): 6706-17.

Postma, F. R., K. Jalink, et al. (1996). "Sphingosine-1-phosphate rapidly induces Rho-dependent neurite retraction: action through a specific cell surface receptor." *Embo J* 15(10): 2388-92.

Pyne, S, and N. Pyne (2000). "Sphingosine 1-phosphate signalling via the endothelial differentiation gene family of G-protein-coupled receptors." *Pharmacol Ther* 88(2): 115-31.

Pyne, S, and N. J. Pyne (2000). "Sphingosine 1-phosphate signalling in mammalian cells."*Biochem J* 349(Pt 2): 385-402.

Rajan, P. and R. D. McKay (1998). "Multiple routes to astrocytic differentiation in the CNS."*J Neurosci* 18(10): 3620-9.

Rius, R. A., L. C. Edsall, et al. (1997). "Activation of sphingosine kinase in pheochromocytoma PC12 neuronal cells in response to trophic factors." *FEBS Lett* 417(2): 173-6.

Sautin, Y. Y., M. Jorgensen, et al. (2002). "Hepatic oval (stem) cell expression of endothelial differentiation gene receptors for lysophosphatidic acid in mouse chronic liver injury." *J Hematother Stem Cell Res* 11(4): 643-9.

Snyder, E. Y., C. Yoon, et al. (1997). "Multipotent neural precursors can differentiate toward replacement of neurons undergoing targeted apoptotic degeneration in adult mouse neocortex." *Proc Natl Acad Sci USA* 94(21): 11663-8.

Tigyi, G., D. L. Dyer, et al. (1994). "Lysophosphatidic acid possesses dual action in cell proliferation." *Proc Natl Acad Sci USA* 91(5): 1908-12.

Weiner, J. A., J. H. Hecht, et al. (1998). "Lysophosphatidic acid receptor gene vzg-1/1pA1/edg-2 is expressed by mature oligodendrocytes during myelination in the postnatal murine brain." *J Comp Neurol* 398(4): 587-98.

Williams, B. P., J. K. Park, et al. (1997). "A PDGF-regulated immediate early gene response initiates neuronal differentiation in ventricular zone progenitor cells." *Neuron* 18(4): 553-62.

Yamazaki, Y., J. Kon, et al. (2000). "Edg-6 as a putative sphingosine 1-phosphate receptor coupling to Ca(2+) signaling pathway." *Biochem Biophys Res Commun* 268(2): 583-9.

Zhang, R. L., Z. G. Zhang, et al. (2001). "Proliferation and differentiation of progenitor cells in the cortex and the subventricular zone in the adult rat after focal cerebral ischemia." *Neuroscience* 105(1): 33-41.

Zwick, E., P. O. Hackel, et al. (1999). "The EGF receptor as central transducer of heterologous signalling systems." *Trends Pharmacol Sci* 20(10): 408-12.

We claim:

1. A method of modulating the activity of an S1P, LPA, EDG receptor or a combination thereof, on an adult neural stem cell (NSC) comprising the step of exposing the cell expressing the receptor to a modulator agent selected from the group consisting of S1P, LPA or EDG receptor agonist, wherein the exposure induces increased NSC proliferation compared to untreated cells, and wherein the NSC is derived from adult brain, neural cell culture or a neurosphere.

2. The method of claim 1 wherein the EDG receptor is selected from the group consisting of EDG1, EDG2, EDG3, EDG4, EDG5 and EDG8.

3. A method for stimulating mammalian adult NSC proliferation comprising the step of contacting a cell population comprising mammalian adult NSC to an agent selected from the group consisting of an S1P, LPA or EDG receptor agonist to form a treated NSC, wherein the treated NSC cell shows increased proliferation compared to untreated cells, and wherein the NSC is derived from lateral ventricle wall of a mammalian brain.

4. The method of claim 3 wherein the EDG receptor is selected from the group consisting of EDG1, EDG2, EDG3, EDG4, EDG5 and EDG8.

5. A method for stimulating primary adult mammalian NSC to proliferate to form neurospheres comprising contacting the cell with an agent selected from the group consisting of an S1P, LPA or EDG receptor agonist to produce a proliferating NSC.

6. The method of claim 5 wherein the EDG receptor is selected from the group consisting of EDG1, EDG2, EDG3, EDG4, EDG5 and EDG8.

7. A method of enhancing neural stem cell proliferation in a patient having a central nervous system disorder comprising the step of infusing an S1P, LPA or EDG receptor agonist thereof into the patient, wherein neural stem cells show increased proliferation compared to untreated cells.

8. The method of claim 7 wherein the EDG receptor is selected from the group consisting of EDG1, EDG2, EDG3, EDG4, EDG5 and EDG8.

9. The method of claim 7 wherein the infusion is selected from the group consisting of intraventricular, intravenous, sublingual, subcutaneous and intraarterial infusion.

* * * * *